United States Patent
Cheng et al.

(10) Patent No.: US 11,337,616 B2
(45) Date of Patent: *May 24, 2022

(54) FETAL HEART RATE EXTRACTION FROM MATERNAL ABDOMINAL ECG RECORDINGS

(71) Applicant: KONINKLIJKE PHILIPS N.V., Eindhoven (NL)

(72) Inventors: Limei Cheng, Irvine, CA (US); Eric Thomas Carlson, New York, NY (US); Srinivasan Vairavan, Ossining, NY (US); Minnan Xu, Sleepy Hollow, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 199 days.

This patent is subject to a terminal disclaimer.

(21) Appl. No.: 16/577,425

(22) Filed: Sep. 20, 2019

(65) Prior Publication Data

US 2020/0022597 A1 Jan. 23, 2020

Related U.S. Application Data

(63) Continuation of application No. 14/913,700, filed as application No. PCT/IB2014/063984 on Aug. 20, 2014, now Pat. No. 10,531,801.

(Continued)

(51) Int. Cl.
*A61B 5/02* (2006.01)
*A61B 5/024* (2006.01)
(Continued)

(52) U.S. Cl.
CPC ........ *A61B 5/02411* (2013.01); *A61B 5/0255* (2013.01); *A61B 5/316* (2021.01);
(Continued)

(58) Field of Classification Search
CPC . A61B 5/02411; A61B 5/0472; A61B 5/0456; A61B 5/04017; A61B 5/0255;
(Continued)

(56) References Cited

U.S. PATENT DOCUMENTS 7,340,289 B2 3/2008 Kandori
8,116,857 B2 2/2012 Kimura
(Continued)

FOREIGN PATENT DOCUMENTS

WO 03/028550 4/2003
WO 2011/003132 1/2011

OTHER PUBLICATIONS

Abboud et al., "Real-time abdominal fetal ECG recording using a hardware correlator", Computers in Biology and Medicine, vol. 22, No. 5, Sep. 1, 1992.
(Continued)

*Primary Examiner* — Rex R Holmes

(57) ABSTRACT

System (10) for extracting a fetal heart rate from at least one maternal signal using a computer processor (26). The system includes sensors (12-18) attached to a patient to receive abdominal ECG signals and a recorder and digitizer (20) to record and digitize each at least one maternal signal in a maternal signal buffer (22A-22D). The system further includes a peak detector (40) to identify candidate peaks in the maternal signal buffer. The signal stacker (42) of the system stacks the divides at least one maternal signal buffer into a plurality of snippets, each snippet including one candidate peak and a spatial filter (44) to identify and attenuate a maternal QRS signal in the plurality of snippets of the maternal signal buffer, the spatial filter including at least one of principal component analysis and orthogonal projection, to produce a raw fetal ECG signal which is stored in a raw fetal ECG buffer. The system further includes a fetal QRS identifier (46) for identifying peaks in the raw fetal
(Continued)

ECG buffer by at least one of principal component analysis and a peak-detector followed by rule based fQRS extraction and a merger (48) to calculate and merge the fetal heart rate from the identified peaks.

11 Claims, 15 Drawing Sheets

Related U.S. Application Data

(60) Provisional application No. 61/918,960, filed on Dec. 20, 2013, provisional application No. 61/875,209, filed on Sep. 9, 2013.

(51) Int. Cl.
| | |
|---|---|
| *A61B 5/0255* | (2006.01) |
| *A61B 5/00* | (2006.01) |
| *A61B 5/316* | (2021.01) |
| *A61B 5/344* | (2021.01) |
| *A61B 5/352* | (2021.01) |
| *A61B 5/366* | (2021.01) |
| *A61B 5/327* | (2021.01) |
| *A61B 5/364* | (2021.01) |

(52) U.S. Cl.
CPC .............. *A61B 5/344* (2021.01); *A61B 5/352* (2021.01); *A61B 5/366* (2021.01); *A61B 5/4362* (2013.01); *A61B 5/7203* (2013.01); *A61B 5/7253* (2013.01); *A61B 5/02405* (2013.01); *A61B 5/327* (2021.01); *A61B 5/364* (2021.01); *A61B 5/725* (2013.01)

(58) Field of Classification Search
CPC ... A61B 5/0444; A61B 5/7253; A61B 5/4362; A61B 5/7203; A61B 5/02405; A61B 5/0468; A61B 5/04028; A61B 5/725
See application file for complete search history.

(56) References Cited

U.S. PATENT DOCUMENTS

| | | | |
|---|---|---|---|
| 10,531,801 B2* | 1/2020 | Cheng | .................... A61B 5/316 |
| 2005/0267376 A1 | 12/2005 | Marossero et al. | |
| 2013/0070792 A1 | 3/2013 | Shoaib et al. | |

OTHER PUBLICATIONS

Karvounis, et al., "A Method for Fetal Heart Rate Extraction Based on Time-Frequency Analysis", Computer-Based Medical Systems, 2006.
Kotas, et al., "Towards noise immune detection of fetal QRS complexes", Computer Methods and Programs in Biomedicine, vol. 97, No. 3, Mar. 1, 2010.
Xeuyan Xu, et al., "Automatic detection of artifacts in heart period data", Journal of Electrocardiology, vol. 34, No. 4, Oct. 1, 2001.
Vullings et al., "Dynamic segmentation and linear prediction for maternal ECG removal in antenatal abdominal recordings", Physiological Measurement, vol. 30, No. 3, Mar. 1, 2009.
Abboud, et al,. "Quantification of the fetal electrocardiogram using averaging technique", Computers in Biology and Medicine, vol. 20, No. 3, Jan. 1, 1990.
Ruben Marti N-Clemente, et al., "Fast Technique for Noninvasive Fetal ECG Extraction", IEEE Transactions on Biomedical Engineering, IEEE Service Center, vol. 58, No. 2, Feb. 1, 2011.
James, et al., "Topical Review; Independent component analysis for biomedical signals", Physiological Measurement, Institute of Physics Publishing, vol. 26, No. 1, Feb. 1, 2005.
Masoumeh Haghpanahi, et al., "Fetal ECG extraction from abdominal recordings using array signal processing", 2012 Computing in Cardiology, Jan. 1, 2013.
Sameni, "Extraction of Fetal Cardiac Signals from an Array of Maternal Abdominal Recordings", Institut Polytechnique de Grenoble, Grenoble, France, Jul. 2008.
McCubbin, et al., "Optimal Reduction of MCG in Fetal MEG Recordings", IEEE Transaction on Biomedical Engineering, vol. 53, No. 8, Aug. 2006.
Ulusar, et al., "Adaptive Rule Based Fetal QRS Complex Detection Using Hilbert Transform", 31st Annual International Conference of the IEEE EMBS, Sep. 2009.
Vrba, et al., "Removal of interference from fetal MEG by frequency dependent subtraction", Neuroimage. Feb. 1, 2012; 59(3): 2475-2484.
Castells, et al., "Estimation of Atrial Fibrillatory Waves from One-Lead ECGs Using Principal Component Analysis Concepts", Computers in Cardiology 2004;31:413-416.
Ghodsi, et al., "Extracting fetal heart signal from noisy maternal ECG by multivariate singular spectrum analysis", Statistics and its interface, vol. 3, No. 3, pp. 399-411, 2010.

* cited by examiner

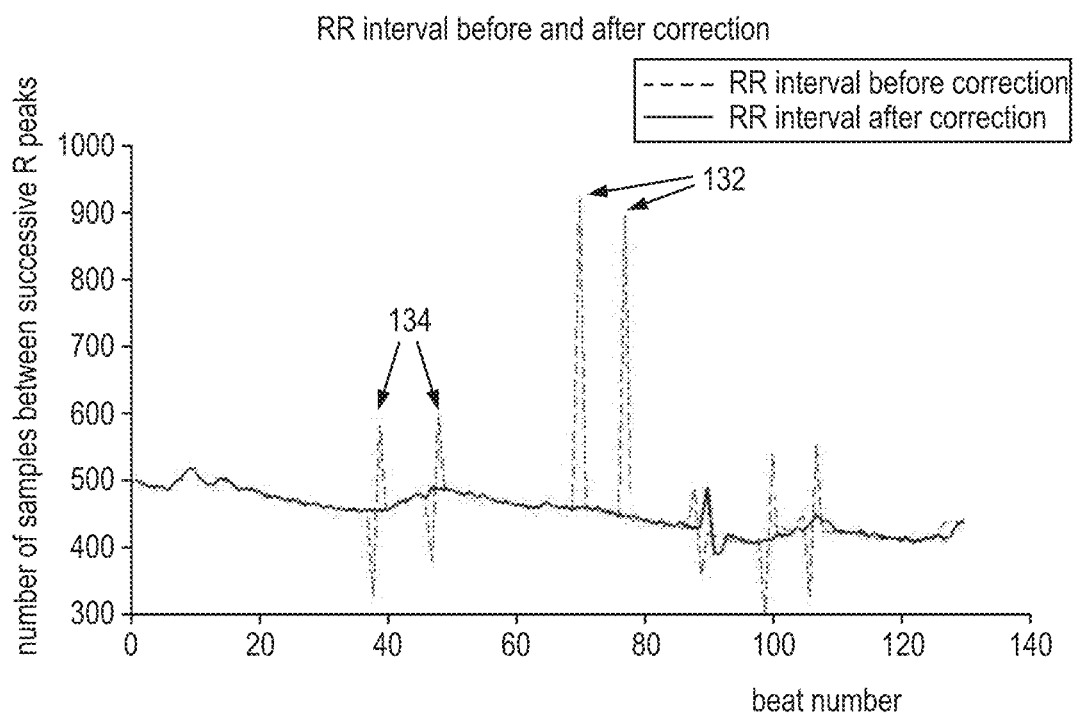
FIG. 21
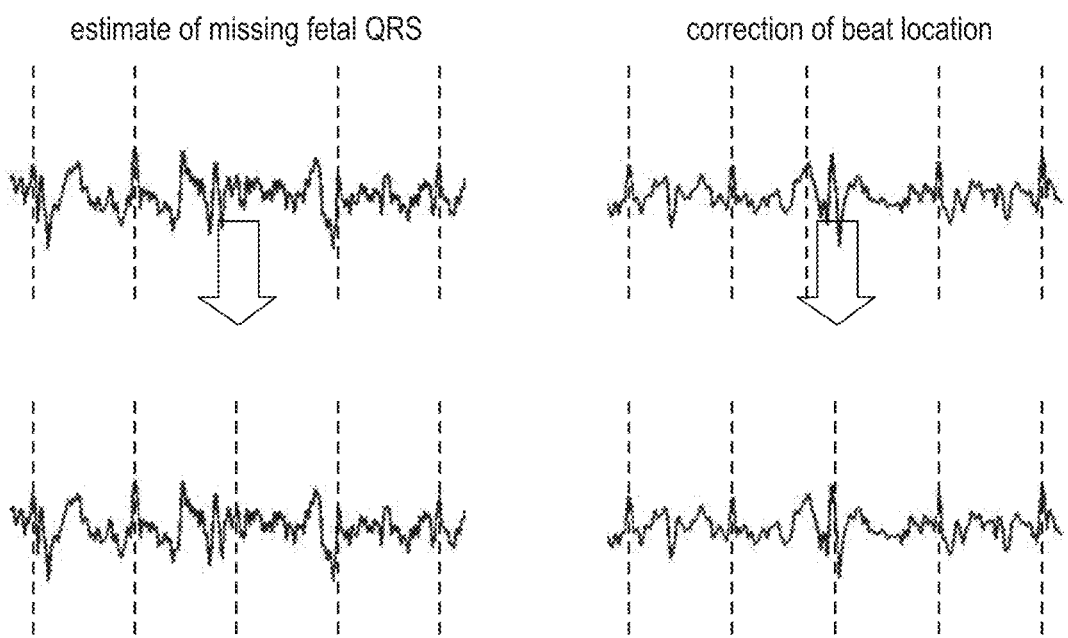
FIG. 22
FIG. 23

FETAL HEART RATE EXTRACTION FROM MATERNAL ABDOMINAL ECG RECORDINGS

CROSS-REFERENCE TO PRIOR APPLICATIONS

This application is a continuation application of U.S. National Phase application under 35 U.S.C. § 371, Ser. No. 14/913,700, filed on 23 Feb. 2016, which claims the benefit of International Application Serial No. PCT/IB2014/063984, filed on 20 Aug. 2014, which claims the benefit of U.S. Provisional Application No. 61/875,209, filed on 9 Sep. 2013, and 61/918,960, filed on 20 Dec. 2013. These applications are hereby incorporated by reference herein.

The present application relates generally to extracting a fetal heart rate from maternal abdominal electrocardiogram (ECG) recordings. It finds particular application in conjunction with the usage of spatial filtering and adaptive rule-based fetal QRS detection and will be described with particular reference thereto. However, it is to be understood that it also finds application in other usage scenarios and is not necessarily limited to the aforementioned application.

Heart defects are among the most common birth defects and the leading cause of birth defect-related deaths. Every year, about one out of 125 babies are born with some form of congenital heart defects. Congenital heart defects originate in early stages of pregnancy when the heart is forming and they can affect any of the parts or functions of the heart. Cardiac anomalies may occur due to a genetic syndrome, inherited disorder, or environmental factors such as infections or drug misuse. However, except for during labor, fetal electrocardiography has not proved an effective tool for imaging specific structural defects.

Detection and analysis of fetal cardiac signals are essential components of fetal health monitoring and have various applications in monitoring of fetal arrhythmia, fetal behavioral state and etc., but fetal electrocardiography has been confined to more global issues such as general ischemia due to specific fetal positioning that chokes the umbilical cord. The reason for this limitation is that the noninvasive fetal electrocardiogram (ECG) is contaminated by fetal brain activity, myographic (muscle) signals (from both the mother and fetus), movement artifacts and multiple layers of different dielectric biological media through which the electrical signals must pass. Fetal ECG is much weaker than the other interfering bio-signals (maternal cardiac signals, uterine contraction) and often contaminated by fetal brain activity, myographic (muscle) signals (from both the mother and fetus), and movement artifacts. Continuous fetal heart rate (FHR) monitors are hoped to reduce undiagnosed fetal hypoxia, but the outputs are often unreliable and difficult to interpret, resulting in increased Caesarean section rates of deliveries of healthy infants.

The most accurate method for measuring FHR is direct fetal electrocardiographic (FECG) using a fetal scalp electrode which is only possibly used in labor but not commonly used in clinical due to its associated risk. Non-invasive FECG monitoring is measured through electrodes placed on expecting mother's abdomen. This method can be used after the middle of the fourth month of pregnancy with negligible risk. However, it is often difficult to detect the FHR in the abdominal ECG signal, since the maternal ECG is usually of greater amplitude in them and R-peaks of maternal ECG often overlap with the R-peaks of fetal ECG. Using sophisticated signal processing techniques have improved accuracy in FHR estimation. There are still great deals of room for improvement.

Fetal monitoring today is based on the fetal heart rate and does not incorporate characteristics of the fetal ECG (fECG) waveform characteristics that are the cornerstone of cardiac evaluation of both children and adults. The primary reason for the exclusion of this most critical source of information from clinical practice is that the technology to reliably measure fECG is largely unavailable. As a consequence, research correlating ECG characteristics to neonatal outcomes has not been done on a large scale. The maternal ECG as discussed is a potential noise, which corrupts fetal ECG.

Existing ECG analysis techniques are generally tuned for situations where the ECG signal dominates the noise present in a recording channel. In situations where this is not the case, for example when using lower-cost ECG equipment or when attempting to record fetal heart beat from abdominal electrodes placed on the mother, the signal deviations due to noise can become indistinguishable from signal deviations due to the electrical activity of the heart.

Extraction of a reliable fetal heart rate and fetal ECG signals would enable the clinicians in an early detection of cardiac abnormalities and help them to prescribe proper medications in time, or to consider the necessary precautions during delivery or after birth. Despite advances in adult electrocardiography and signal processing techniques, the analysis of fetal ECGs is still in its infancy. The clinical potential of abdominal fECG monitoring by placing electrodes over mother's abdomen in antepartum (prior to labor) has been hampered by difficulties in obtaining a reliable fECG. There is a need for a method of extracting the fECG from the maternal ECG.

The present application provides new and improved methods, which overcome the above-referenced problems and others.

In accordance with one aspect, a system for extracting a fetal heart rate from at least one maternal signal using a computer processor is provided. The system includes sensors attached to a patient to receive abdominal ECG signals and a recorder and digitizer to record and digitize each at least one maternal signal in a maternal signal buffer. The system further includes a peak detector to identify candidate peaks in the maternal signal buffer. The signal stacker of the system stacks and divides at least one maternal signal buffer into a plurality of snippets, each snippet including one candidate peak and a spatial filter identifies and attenuates a maternal QRS signal in the plurality of snippets of the maternal signal buffer, the spatial filter including at least one of principal component analysis and orthogonal projection, to produce a raw fetal ECG signal which is stored in a raw fetal ECG buffer. The system further includes a fetal QRS identifier for identifying peaks in the raw fetal ECG buffer by at least one of principal component analysis and a peak-detector followed by rule based fQRS extraction and a merger to calculate and merge the fetal heart rate from the identified peaks.

In accordance with another aspect, a method of extracting a fetal heart rate from at least one maternal signal is provided. The method includes recording and digitizing at least one maternal signal in a maternal signal buffer and identifying candidate peaks in the maternal signal buffer. The method divides the at least one maternal signal buffer into a plurality of snippets, each snippet including one candidate peak. A maternal QRS signal is identified and attenuated by spatial filtering in the plurality of snippets of the maternal signal buffer. The spatial filter includes at least a principal component analysis or orthogonal projection and produces a raw fetal ECG signal, which is stored in a raw fetal ECG buffer. The peaks in the raw fetal ECG buffer are identified by principal component analysis or a peak-detector followed by rule based fQRS extraction and the fetal heart rate is identified from the peaks.

In accordance with another aspect, a module for extracting a fetal heart rate from at least one maternal signal is provided. The module includes a recorder and digitizer which records and digitizes at least one maternal signal in a maternal signal buffer. The module also includes a processor configured to identify candidate peaks in the maternal signal buffer and divide the at least one maternal signal buffer into a plurality of snippets, each snippet including one candidate peak. The processor is further configured to identify and attenuate, by spatial filtering, a maternal QRS signal in the plurality of snippets of the maternal signal buffer with the spatial filter including at least one of principal component analysis and orthogonal projection wherein the spatial filtering produces a raw fetal ECG signal which is stored in a raw fetal ECG buffer. The processor then identifies peaks in the raw fetal ECG buffer by at least one of principal component analysis and a peak-detector followed by rule based fQRS extraction and a calculator calculates the fetal heart rate from the identified peaks.

One advantage resides in improved fetal ECG readings from abdominal ECG recordings using orthogonal projection or principal component analysis.

Another advantage resides in improved reliability of continuous fetal heart rate monitoring and reading interpretation.

Another advantage resides in improved identification of cardiac signals in a low signal-to-noise ratio ECG such as a fetal heart beat detection.

Another advantage resides in improved clinical workflow.

Another advantage resides in improved patient care.

Still further advantages of the present invention will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 21 illustrates an RR interval before and after correction.

FIG. 22 illustrates an RR interval denoting where missing beats are likely.

FIG. 23 illustrates an RR interval denoting where peaks are misidentified.

The present application is directed to a method for improved fetal heart rate extraction and interpretation. The invention disclosure is inspired by the insight that current methods for monitoring fetal heart rates are unreliable and difficult to interpret resulting in increased caesarean sections for health infants. Presently, the most accurate method for measuring fetal heart rates is direct fetal electrocardiographic using a fetal scalp electrode, which is only typically used during labor due to its associated risks during a routine pregnancy exam. Non-invasive fetal electrocardiographic monitoring is measured through electrodes placed on the mother's abdomen, however, it is often difficult to detect the fetal heart rate since the maternal ECG is usually more prevalent.

The present application presents an improved algorithm for fetal heart rate extraction from abdominal fECG recording using spatial filtering, such as Principal component analysis and orthogonal projection techniques for maternal ECG attenuation and PCA clustering. Additionally, the present invention utilizes adaptive rule based fetal QRS detection for the extraction of the fetal heart rate.

Figure 1:
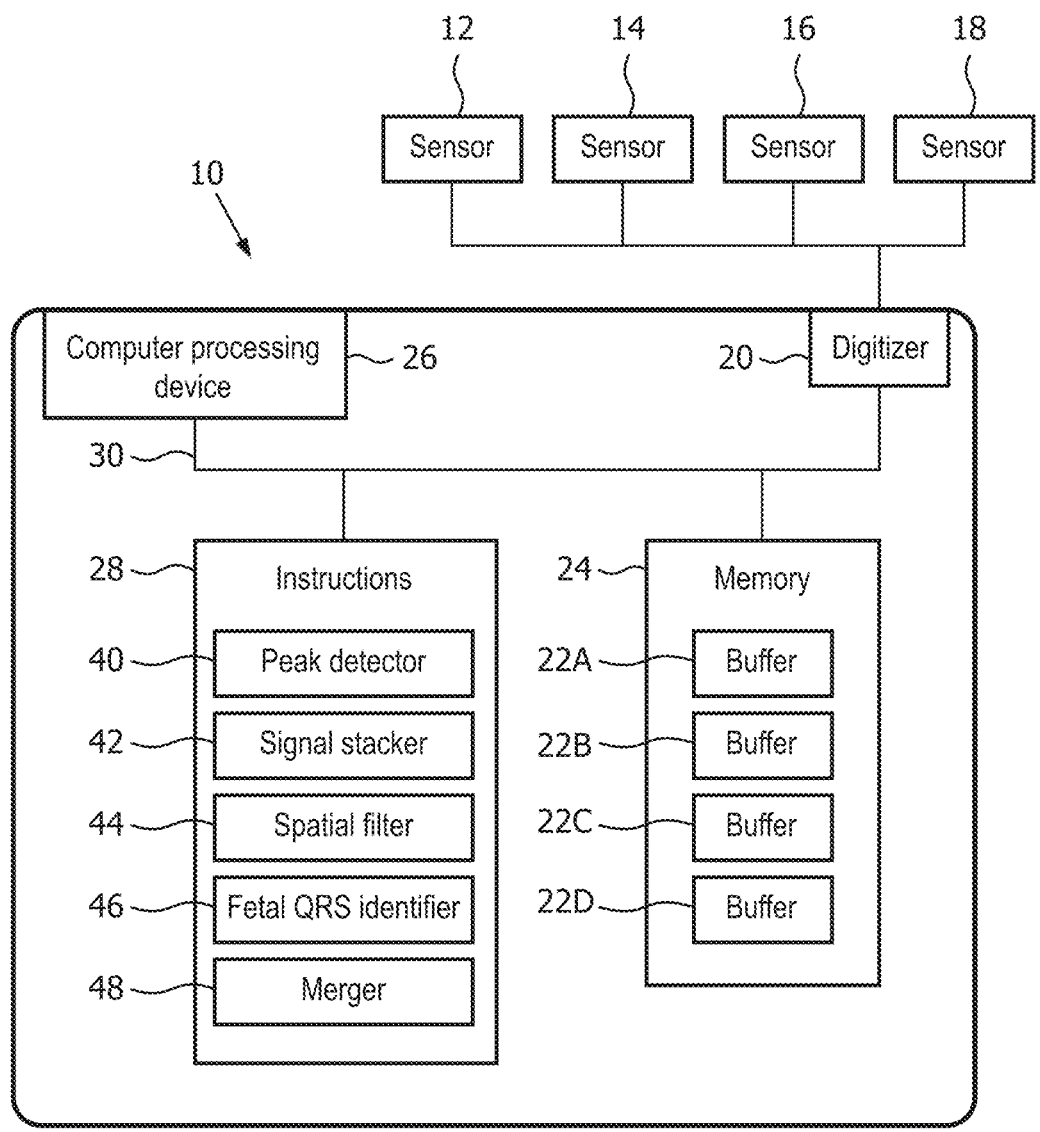
FIG. 1 illustrates a fetal heart rate extraction system.

With reference to FIG. 1, a fetal heart rate extraction system 10 receives abdominal ECG signals from sensors 12-18 attached to a patient (e.g., a pregnant woman). The sensors 12-18 provide signals, which are digitized by an A/D converter digitizer 20 and stored in buffers 22A-22D. Each sensor may provide a signal stored in its own respective buffer. The buffers 22A-22D are part of a memory 24. The system 10 includes a computer-processing device 26 (or "processor") to execute instructions stored in an instruction memory 28. The instruction memory 28, the data memory 24, the digitizer 20, and the processor 26 are connected by a data bus 30.

The system 10 may include one or more dedicated or general-purpose computing devices, such a server computer or a laptop computer with an associated display device and a user input device, such as a keyboard and/or cursor control device (not shown). The memories 24, 28 may be separate or combined and may represent any type of computer readable memory such as random access memory (RAM), read only memory (ROM), magnetic disk or tape, optical disk, or flash memory. The processor can be variously embodied, such as by a single-core processor, a dual-core processor (or more generally by a multiple-core-processor), a digital processor and cooperating math coprocessor, a digital controller, and the like.

The term "software" as used herein is intended to encompass any collection or set of instructions executable by a computer or other digital system so as to configure the computer or other digital system to perform the task that is the intent of the software. The term "software" as used herein is intended to encompass such instructions stored in the storage medium such as RAM, a hard disk, optical disk, or so forth, as is also intend to encompass so-called "firmware" that is software stored on a ROM or so forth. Such software may be organized in various ways, and may include software components organized as libraries, Internet-based programs stored on a remote server or so forth, source code, interpretive code, directly executable code, and so forth. It is contemplated that the software may invoke system-level code or calls to other software residing on a server or other location to perform certain functions.

In one embodiment, the system 10 is configured by instructions in the memory 28 to embody a peak detector 40, a signal stacker 42, a spatial filter 44 (including a principal component analyzer and a orthogonal projection analyzer), a fetal QRS identifier 46 (including a second principal component analyzer and adaptive rule based analyzer), and a merger 48.

Figure 2:
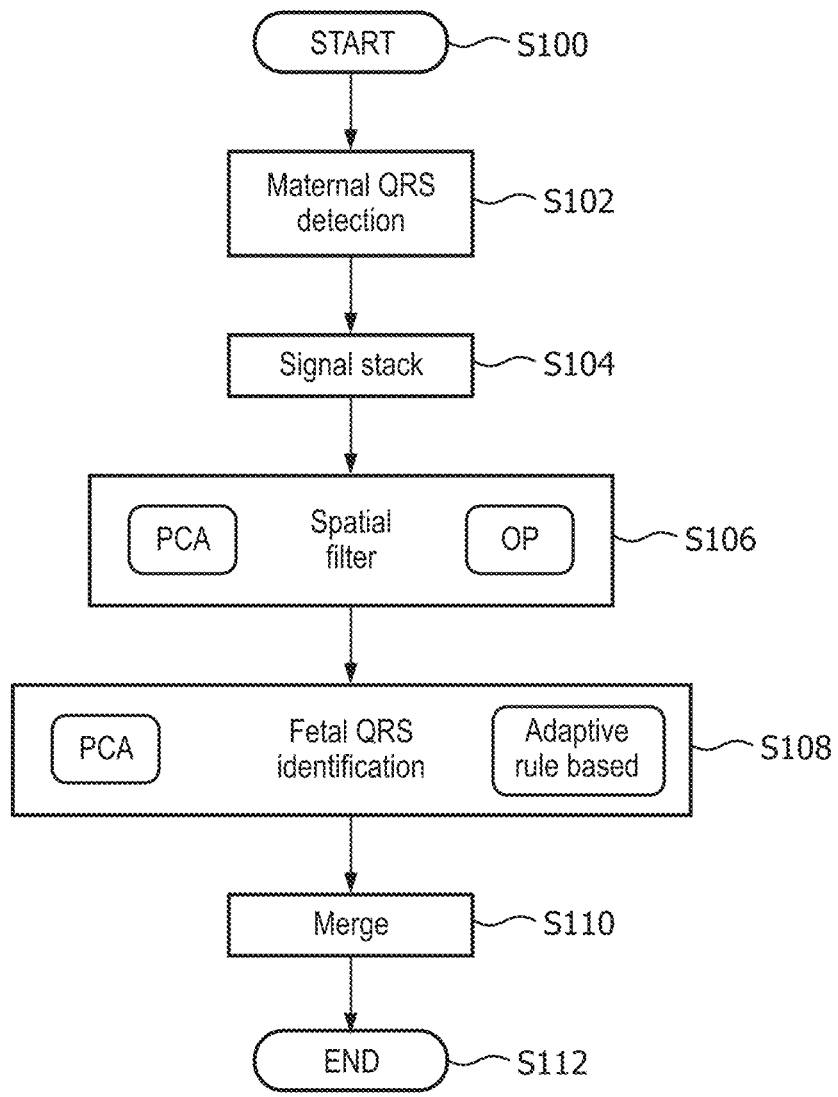
FIG. 2 illustrates a flowchart diagram for detecting a fetal heart rate from an abdominal fECG.

FIG. 2 shows a method in accordance with one embodiment. The steps are, in one embodiment, performed by the computer processor 26 under control of the instructions stored in the memory 28. The method or software modules starts at S100.

At S102, a maternal heart rate is detected in at least one maternal ECG channel. This includes recording and digitizing each ECG channel, storing the digital information in a buffer, filtering the signal in the buffer, and then detecting peaks. Step S102 is explained in greater detail with respect to FIG. 3.

At S104, for each channel (buffer), a fixed n-length window is applied around each of the m maternal QRS complexes (each peak detected in step S102). In one embodiment, the window size is 110% of the median RR interval for that channel, with 35% before the R peak and 75% after the R peak. Each channel results in an m×n matrix. This construction increases the spatial resolution even for a single channel data and aids the spatial filtering techniques of PCA and orthogonal projection (OP) to better attenuate maternal QRS.

At S106, spatial filtering is applied to each channel (or to just one channel if only one channel was recorded) to attenuate the maternal QRS. The spatial filtering uses at least one of principal component analysis and orthogonal projection, explained in further detail below. One channel may be processed using both principal component analysis and orthogonal projection to produce two output buffers.

At S108, the fetal QRS is extracted from the buffer. At least one of adaptive rule based fQRS detection and PCA clustering based fQRS detection are used to extract the fetal QRS. Either technique may be applied to the output of S106, yielding four "paths" through S106 and S108. For example, any one signal may be processed using: Maternal ECG attenuation using PCA followed by fetal ECG detection using PCA, Maternal ECG attenuation using PCA followed by fetal ECG detection using adaptive rule based detection, Maternal ECG attenuation using orthogonal projection followed by fetal ECG detection using PCA, and Maternal ECG attenuation using orthogonal projection followed by fetal ECG detection using adaptive rule based detection. These methods of processing may produce four different results for each signal, although, in a preferred embodiment, only three of the paths are used, as explained below.

At S110, the different signals or different results of processing the signals are merged. Because S104 and S106 may produce multiple output buffers, and multiple signals may have been input, merge fQRS is used to combine the output to get an accurate fetal QRS location and hence an accurate fetal heart rate. This step is explained in further detail below.

At S112, the method ends. To summarize FIG. 2, the raw ECG is first filtered and then subjected to maternal ECG attenuation. Maternal ECG attenuation consists of extraction of the maternal QRS signal, signal stacking around the detected maternal QRS, and application of spatial filtering techniques to attenuate the maternal ECG. Maternal ECG attenuation produces a raw fetal ECG signal, which is processed to detect the fetal ECG signal. Adaptive rule based fQRS detection and PCA clustering are used to extract the fetal QRS from the raw fetal ECG system. Each signal may be processed using different combinations of techniques, or multiple signals may be processed.

Maternal QRS Detection

Figure 3:
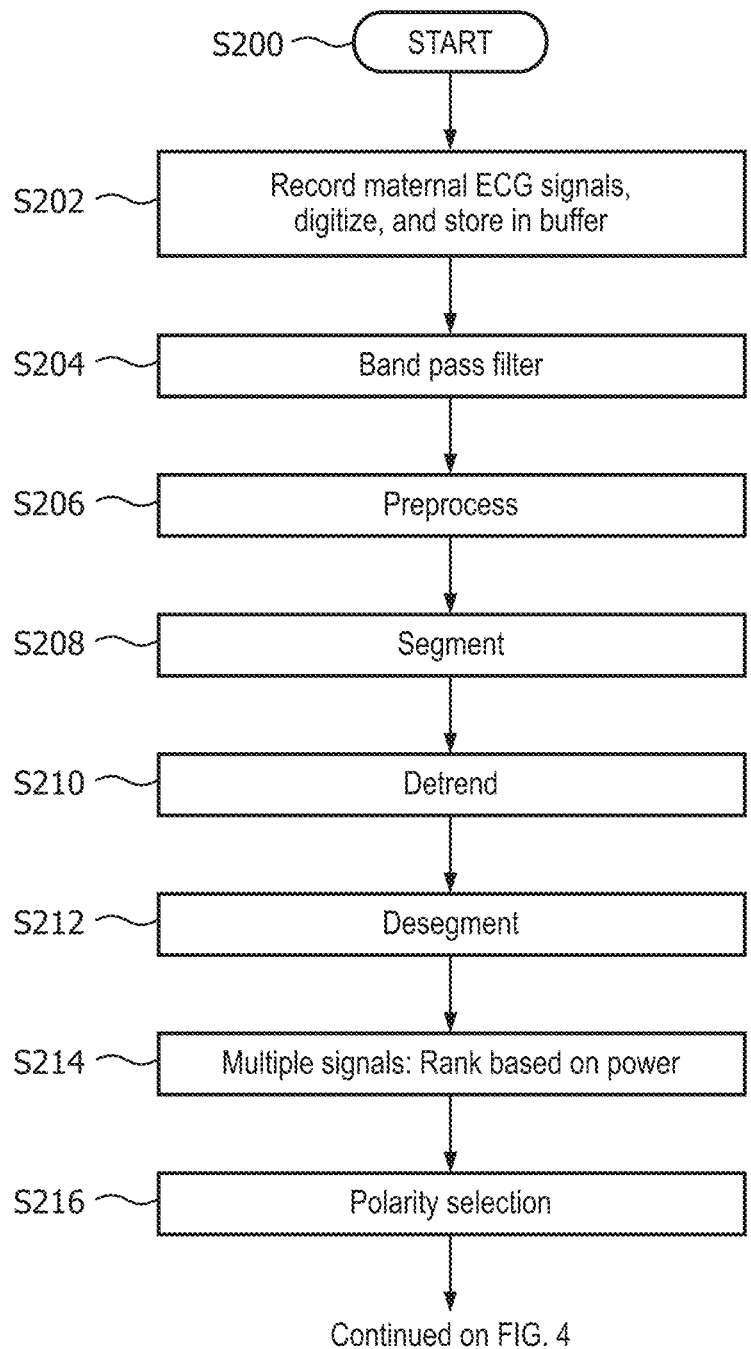
FIG. 3 illustrates a flowchart diagram for maternal QRS detection.
Figure 4:
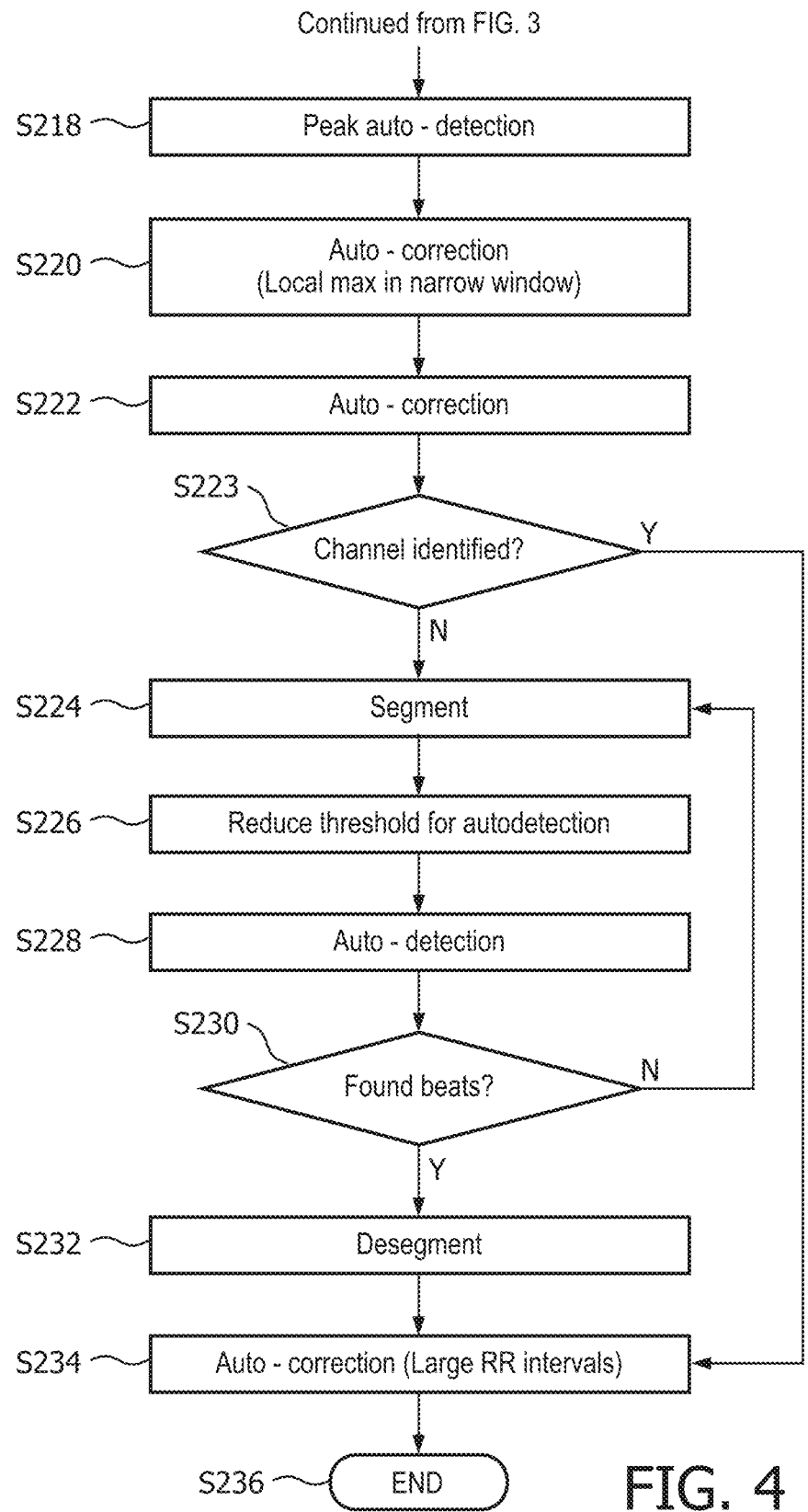
FIG. 4 illustrates a continuation flowchart diagram of FIG. 3 showing the peak detection and auto correction of maternal QRS detection.

FIGS. 3 and 4 show the sub-steps or sub-modules of S102 of FIG. 2.

At S200, step or module S102 of FIG. 1 starts.

At S202, at least one maternal ECG signal is recorded, digitized, and stored in a buffer. In one embodiment, four maternal signals are recorded, though more or fewer are contemplated. In another embodiment, only one maternal signal is recorded. In one embodiment, the maternal ECG is stored in 1 minute buffers. In another embodiment, the buffers may be shorter, e.g., 5, 10, 15, or 30 seconds.

At S204, the raw ECG data is first band-pass filtered between 2-50 Hz (or other filter range, e.g., from 1 Hz to 100 Hz) to remove any baseline-wander and other low-frequency movement artifacts. A median filter could also be used.

At S206, preprocessing begins.

At S208, data for each channel is split into segments of 0.5 sec duration. The duration may be longer or shorter.

At S210, any linear trends are removed.

At S212, the detrended segments are concatenated back together.

At S214, in an embodiment with multiple channels, the channels of pre-processed fECG data are ranked based on 1) the power spectrum of a Fourier transform in descending order with high weight, 2) power of a Hilbert transform in descending order with medium weight, and 3) a standard deviation in ascending order with low weight, respectively. As mentioned before, in one embodiment, there are four channels.

At S216, the polarity of each channel is detected. If the maximum amplitude of the channel is smaller than the absolute value of the minimum amplitude of the channel, then the channel is flipped. The method continues on FIG. 4.

With reference to FIG. 4, at S218, a peak detector is used to detect peaks in the channel. In one embodiment, the peak detector is based on one threshold for searching the channel at local maximums of ECG amplitude and 3 thresholds for derivatives of those indexes of local maximums in which the 3 thresholds partly represent R-R intervals in low, normal and high levels.

At S220, the peaks found in S218 are corrected by searching for a local maximum in a narrow window around the auto-detected peak found in S218.

At S222, the peaks are optionally auto-corrected. In embodiments with multiple channels, the channels are selected which indicate a heart rate (HR, peak numbers of the channel) in a reasonable range (corresponding to 20-150 bpm or preferably 30-132 bpm) and match the other channels with a difference less than 1 bpm. The selected channels are then compared to match the weighted rank in which the highest ranked channel is chosen. At S223, if no channel is selected, the method proceeds to step or module S224. If a channel was selected, the method proceeds to step or module S234.

At S224, the buffer is segmented into shorter ECGs for each channel, e.g. 10.

At S226, the factor of the threshold is reduced.

At S228, auto-detection, similar to S218, is reapplied.

At S230, if the channels which are selected indicate a heart rate (HR, peak numbers of the channel) in a reasonable range (corresponding to 20-150 bpm or preferably 30-132 bpm), processing proceeds to S232. If not, the channels are segmented again at S224.

At S232, the channels are desegmented and processing continues at S234.

At S234, once the channel and correct peak number have been detected, a heart rate is computed from the peak number. A first derivative is also computed from the heart rate. If the absolute value of the first derivative is higher than a threshold, a misplaced peak in will be corrected.

At S236, the method ends. The maternal R peaks in each buffer have been detected. Processing continues at S104 of FIG. 2.

Spatial Filtering: PCA

After the auto-correction of the step or module S102, the signals are stacked at S104, described above. At S106, the stacked buffers are spatially filtered by principal component analysis (PCA) or orthogonal projection. This section describes PCA.

PCA has been used to separate ventricular and atrial components of an adult ECG for estimation of atrial fibrillatory waves. Fetal components can be extracted by applying PCA to the stacked matrix M of maternal beats and subtracting the maternal contributions. The most significant components are related to the main maternal QRST waveform and the interbeat variability that exist in maternal QRST waveform. The remaining components correspond to fetal ECG and sources of contamination. To estimate the fetal ECG (fECG), a mean of the matrix M and the contributions of the top three principal components to that row are subtracted from each row of the matrix M. This removes the maternal ECG. Unstacking the matrix M gives the fetal ECG. A low pass filter can be applied to remove any discontinuity that may have resulted from windowing.

Figure 5:
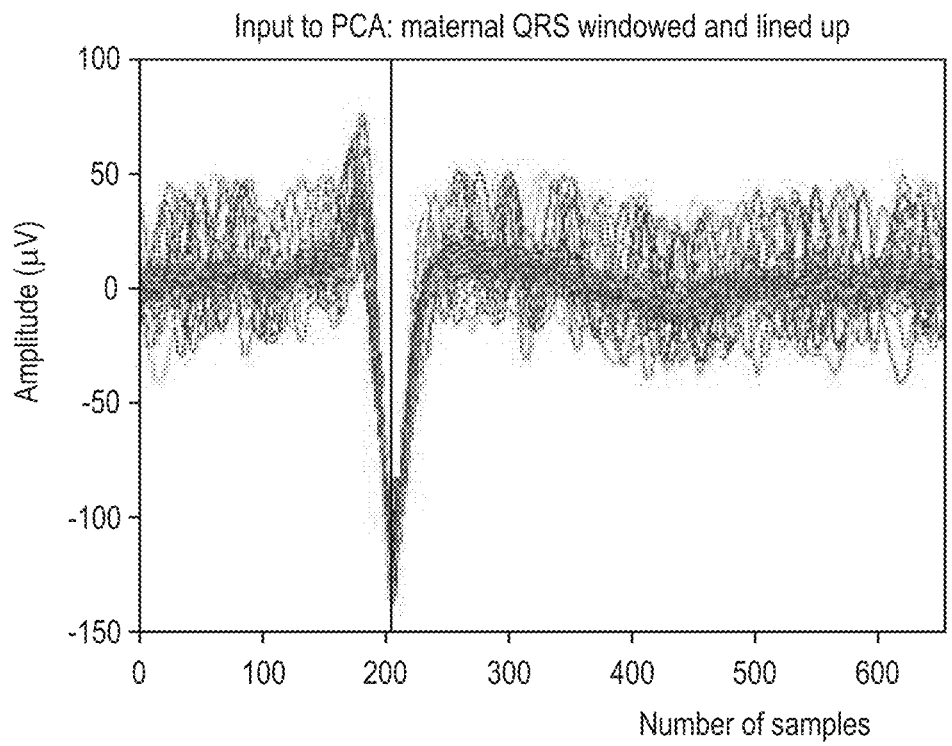
FIG. 5 illustrates the data matrix constructed using the abdominal ECG (AECG) data corresponding to approximately ~200 samples before the maternal QRS peaks and ~450 samples after the maternal peaks.

In one embodiment, the abdominal ECG (AECG) data corresponds to approximately ~200 samples (0.35*mean (RR interval)) before the maternal QRS peaks (detected at step S102) and ~450 samples (0.75*mean (RR interval)) after the maternal peaks. The samples are extracted and stacked in the step or module S104 in a matrix with dimension m×n where m is a number of maternal QRS locations and n is ~650 samples. This construction enables increasing the spatial resolution for each channel and hence enables any spatial filtering technique to better attenuate the maternal QRS. The matrix of stacked beats is shown graphically in FIG. 5.

Figure 6:
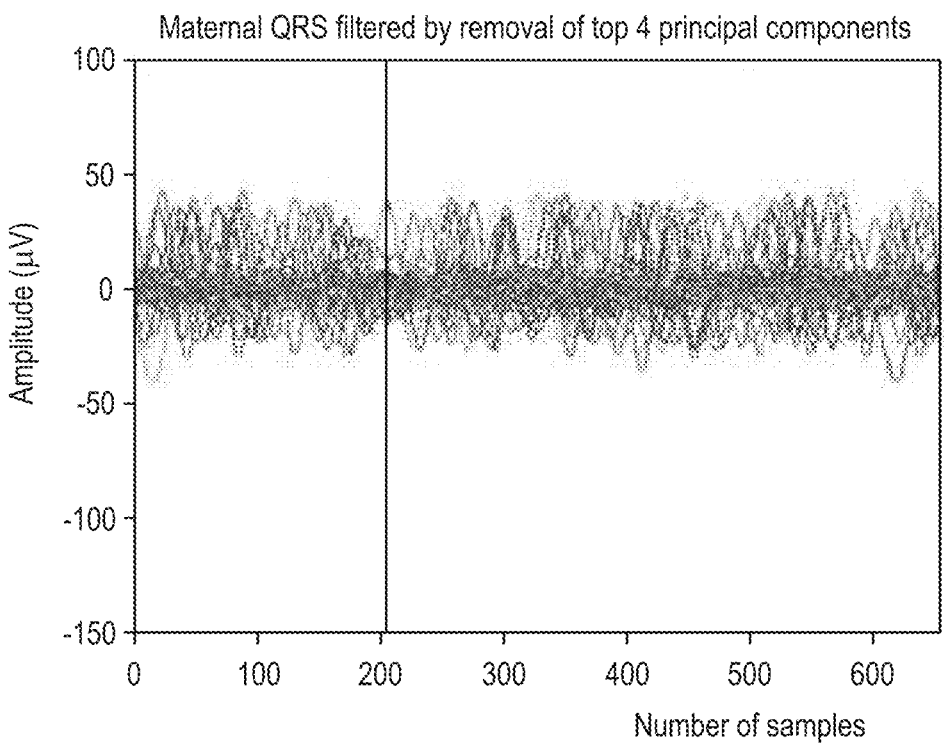
FIG. 6 illustrates the data matrix with the maternal QRS subtracted.
Figure 7:
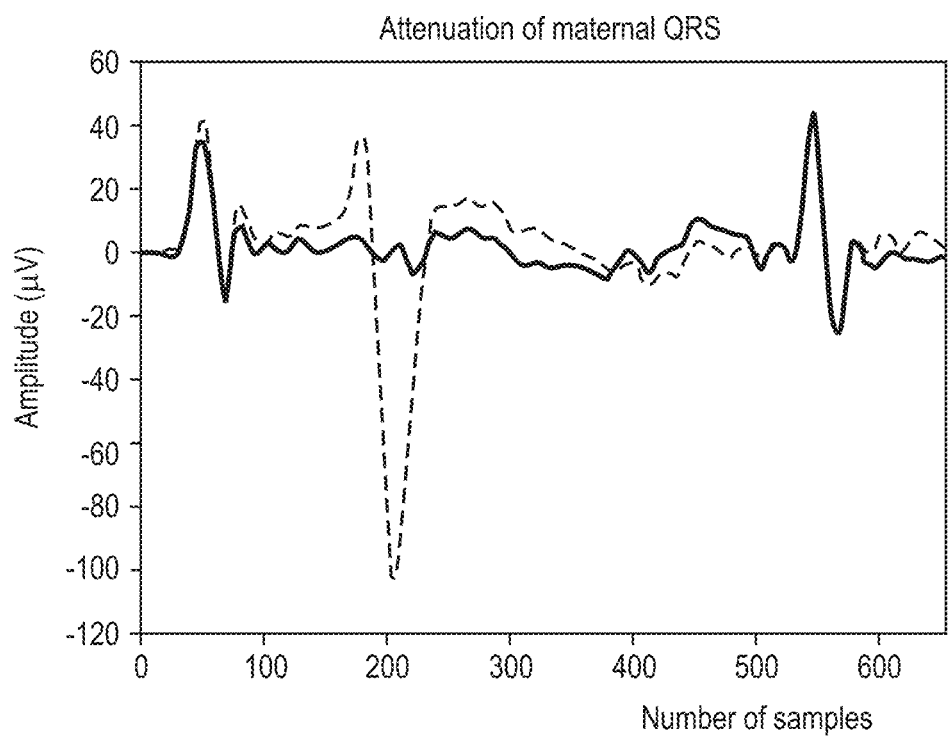
FIG. 7 illustrates before and after maternal attenuation data of a single row in a data matrix when the PCA technique is applied.
Figure 8:
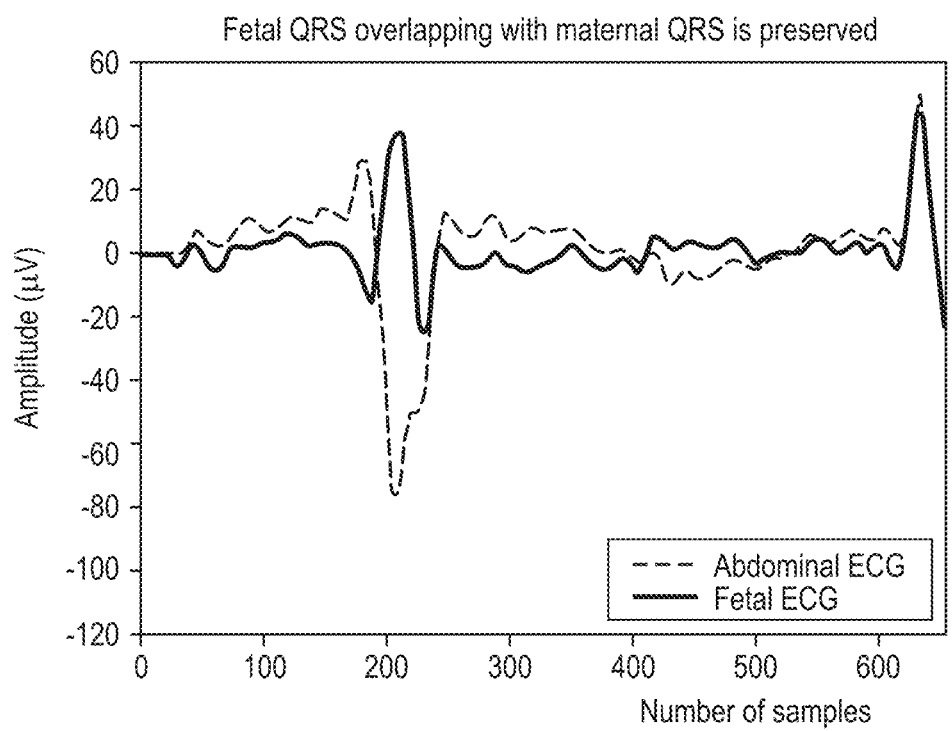
FIG. 8 illustrates a fetal heart beat preserved after attenuation of maternal QRS even when the fetal heart beat overlaps with a maternal QRS.

The data of stacked maternal beats is subjected to PCA to attenuate the maternal ECG. In one embodiment, the mean of the stacked beats along with the next 3 principal components are identified as maternal components. In other embodiments, the mean by itself or the mean plus one or two principal components may be used. In one embodiment, the mean plus three components is used because of the structure of the QRS. A low pass filter may optionally be applied to smooth out any discontinuities resulting from windowing. A set number of principal components are used here to filter out the maternal ECG. However, in another embodiment, one can identify the correct number of components to use for an individual record by looking at how many components represent most of the energy within the signal. Using a smaller number of principal components minimizes attenuation of fetal QRS while using a large number of principal components maximizes removal of maternal QRS. FIG. 6 shows successful attenuation of maternal QRS. FIGS. 7 and 8 show single rows in the data matrix before (dashed) and after (solid) maternal attenuation. FIG. 8 shows that fetal QRS can be preserved even when it overlaps with a maternal QRS complex. Once the maternal components are attenuated via PCA, the remaining components are used to reconstruct the fetal ECG in the step or module S108.

Figure 9:
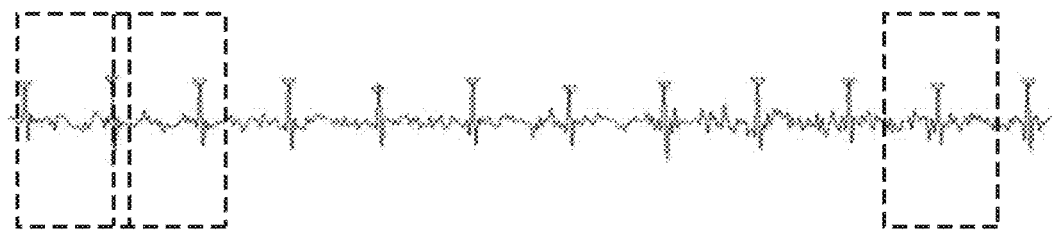
FIG. 9 illustrates shows a fetal ECG (fECG) trace extracted by PCA with the fetal QRS peaks marked with triangles

The above procedure is repeated for all four channels of AECG data. FIG. 9 shows examples of a fetal ECG (fECG) trace extracted by PCA. The fetal QRS peaks (provided for this dataset) are marked with triangles. It can be observed that the proposed approach extracts a clean fECG and hence would enable a robust fetal heart rate extraction and fetal cardiac waveform analysis for in-utero diagnosis. Once the fetal ECG has been extracted for all 4 channels, a rule-based fetal QRS detector or PCA can be used in the step or module S108 to detect fetal heart rates. The results of PCA followed by adaptive rule based filtering are show in Table 1, at the end of this specification, in the row labeled PCA-Adaptive, and for PCA followed by PCA in the row labeled PCA-PCA.

Spatial Filtering: Orthogonal Projection

Orthogonal Projection has been used in attenuation of maternal and fetal Mangenocardiogram (MCG) from fetal Magentoencephalogram (fMEG) and is based on Gram-Schmidt orthogonalization. In the step or module S106 of FIG. 2, the OP is applied to the stacked matrix M to remove maternal contributions. That is, in both OP and PCA, the data is first stacked in the step or module S104. A data point at which the matrix M attains the largest amplitude is chosen as the first maternal ECG signal space vector of dimension m×1, where m is the number of maternal QRS complexes. The choice of the largest amplitude signal space vector can be based on the root mean square (rms) estimate. This vector is projected out from the matrix M. The procedure is then repeated on the residual, and the next signal space vector is selected and projected out, and so on. The vector selection procedure is stopped when the residual drops below a specified threshold, for example, a multiple of the rms noise estimate. As with PCA, the matrix M with maternal contributions removed is un-stacked to give the fetal ECG.

As with PCA, the abdominal ECG (AECG) data corresponds to approximately ~200 samples (0.35*mean (RR interval)) before the maternal QRS locations and ~450 samples (0.75*mean (RR interval)) after the maternal QRS locations, producing 650 samples, shown in FIG. 4, as discussed above.

This data is then subjected to orthogonal projection (OP), based on Gram-Schmidt orthogonalization, to attenuate the maternal ECG. The norm of the maximum vector in the data constructed is extracted and termed as a U matrix with dimension m×1. The constructed data is termed as Avg with dimension m×n. With the application of Gram-Schmidt orthogonalization as described in the equation below, the vector U is projected out of the Avg. In one embodiment, this procedure is repeated until the maximum vector amplitude is less than 5 µvolts. Other thresholds are possible, such as 1, 2, or 10 µvolts.

$$Avg = Avg - \left(\frac{Avg \times U}{U^2}\right) \times U \rightarrow \text{①}$$

Figure 10:
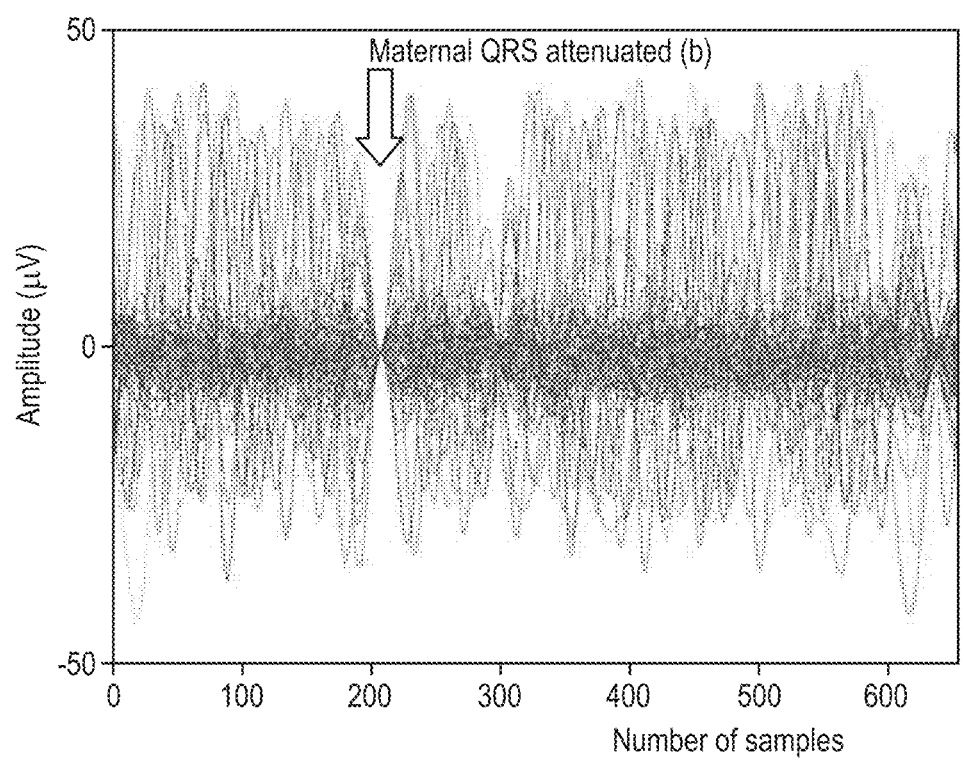
FIG. 10 illustrates the attenuation of a maternal ECG using orthogonal projection technique with the maternal QRS projected out.

The result of this procedure applied to the data of FIG. 4 is shown in FIG. 10. In an embodiment with four channels, the OP is repeated for all four channels of AECG data. Once the fetal ECG has been extracted for all 4 channels, one of PCA and adaptive rule-based fetal QRS detector is used to extract the fetal heart rate. The results shown below in TABLE 1 indicate that OP followed by an adaptive rule based approach (capable of filling the missing fetal QRS locations and also shifting the fetal QRS locations) yields a fetal RR interval measurement of less than 20 across the different datasets. In another embodiment, the OP is followed by PCA.

Figure 11:
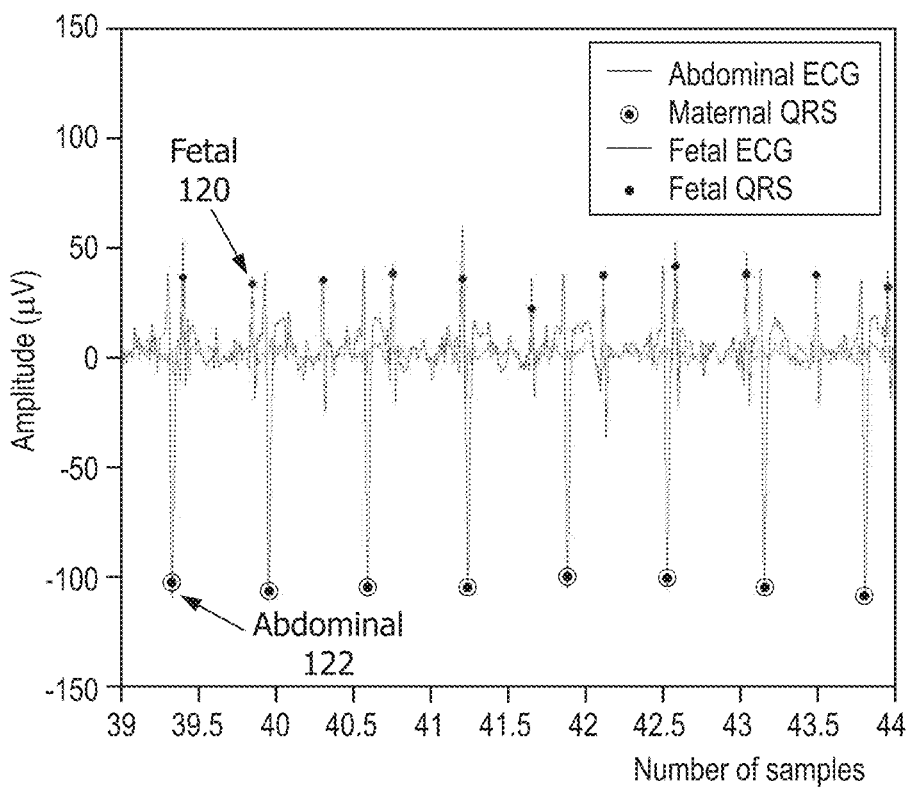
FIG. 11 illustrates the abdominal ECG and fetal ECG trace extracted with the black dot representing the fetal QRS location as annotated based on fetal scalp electrode
Figure 12:
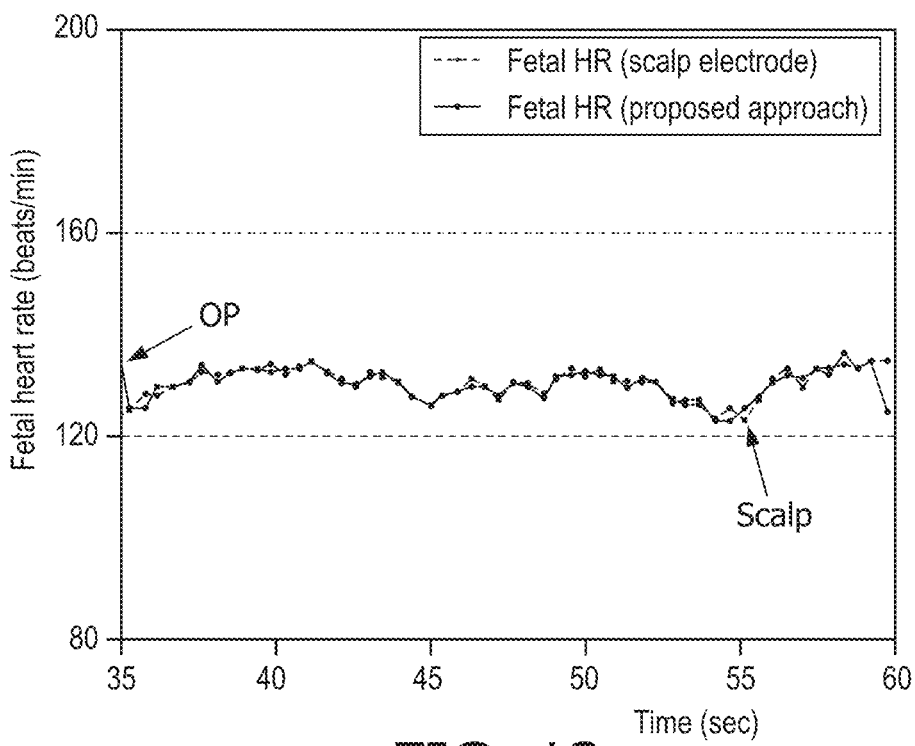
FIG. 12 illustrates the comparison of the fetal heart obtained from fetal ECG (after spatial filtering) to the fetal heart rate obtained from scalp electrode.

FIG. 11 show the abdominal ECG 122 and fetal ECG trace 120 extracted by the proposed approach and the black dot represents the fetal QRS location as annotated based on fetal scalp electrode (used to check the performance of the fetal ECG). Note that the alignment is quite close. FIG. 12 shows the fetal heart rate extracted from the buffers after spatially filtering to remove the maternal QRS, leaving a raw fetal ECG in the buffer. FIG. 12 also includes a fetal heart rate obtained with the fetal scalp electrode, which serves as the gold standard. The PCA or OP method can be used to extract a clean fECG and enable a robust fetal heart rate extraction in the step or module S108.

Figure 13:
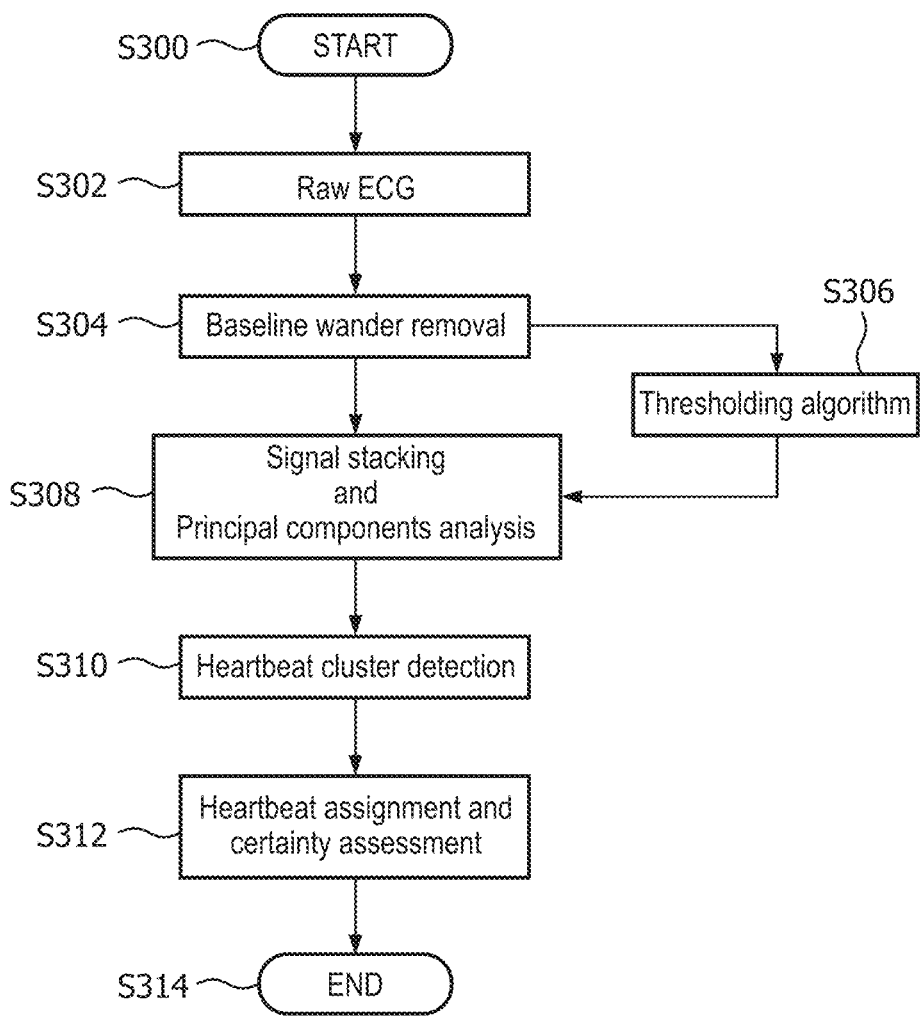
FIG. 13 illustrates a schematic representation of the method for determining heartbeat assignment and certainty assessment information.

PCA Clustering to Identify Fetal QRS (Step or Module S108 of FIG. 2) The sub-steps of the PCA method of the step or module S108 of FIG. 2 are shown in FIG. 13.

At S300, the method starts.

At S302, the data with the maternal QRS attenuated from the step or module S106 is received.

Figure 14:
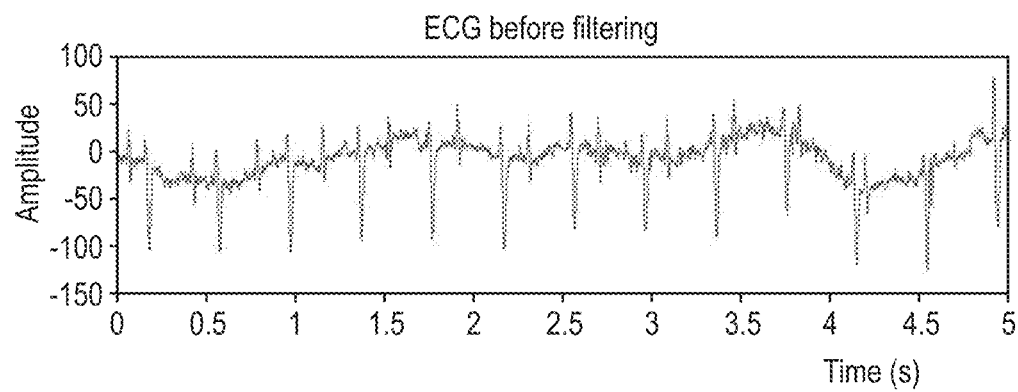
FIG. 14 illustrates the input to a baseline wander removal algorithm.
Figure 15:
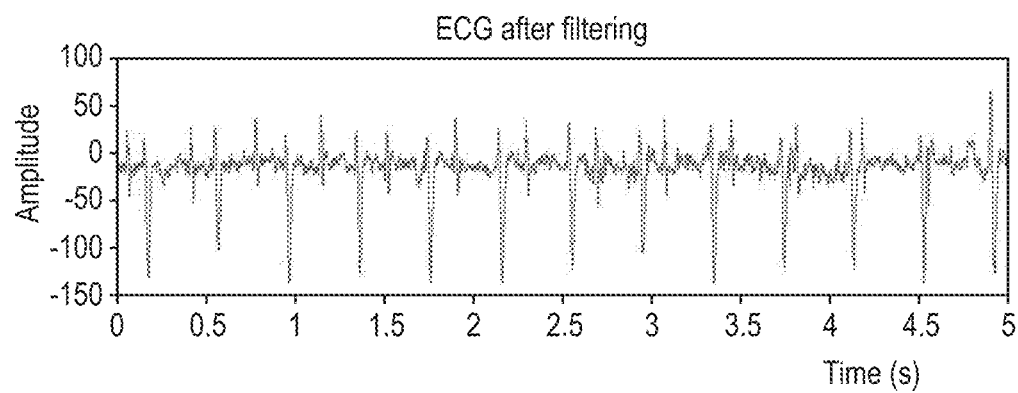
FIG. 15 illustrates the output to a baseline wander removal algorithm.

At S304, a baseline wander removal technique is applied. This may be either a median filter or a band-pass filter (e.g. from 1 Hz to 100 Hz), or other equivalent technique of baseline wander removal. The input (maternally attenuated ECG from S106) is shown in FIG. 14, and the output of such a filter is depicted in FIG. 15.

Figure 16:
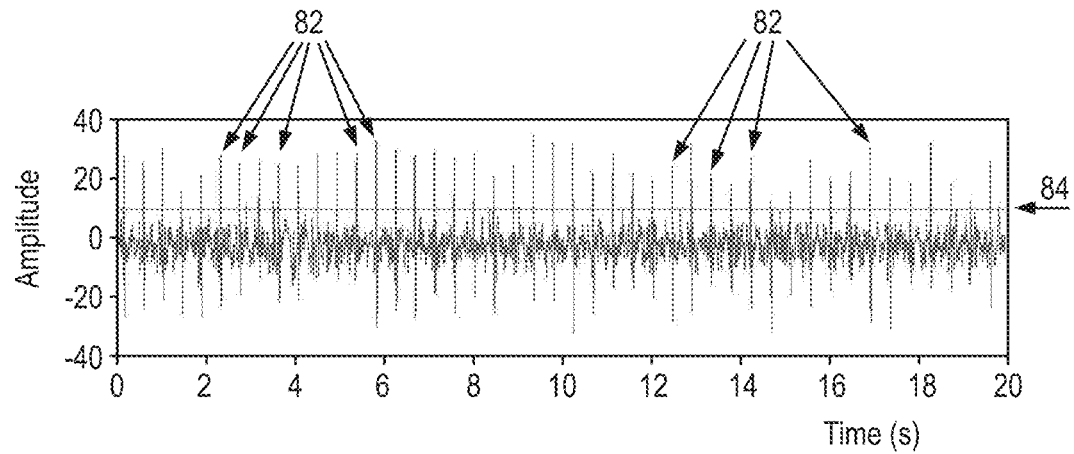
FIG. 16 illustrates the threshold found by the optimized thresholding routine on a 60 s long segment of ECG signal.

At step or module S306, the filtered signal is passed to an automatic thresholding module. The optimized thresholding routine chooses a threshold to minimize the variance of intervals between threshold crossings while constraining the number of threshold crossings to remain in a physiologically plausible range for a fetal heart beat. The threshold level is varied from zero to the maximum signal value, then from zero to the minimum signal value. At each threshold value the number of threshold crossings is recorded, along with the times between threshold crossings and standard deviations of times between threshold crossings. The assumption behind this method is that the R peaks of the desired cardiac components will deviate from baseline more than the majority of the contributions from a normally distributed noise signal. In this case, an optimal threshold value is one where the standard deviation of threshold-crossing intervals is minimized (threshold crossing intervals that are primarily from noise will have larger standard deviations than those from a regular heart beat), with the constraint that the number of threshold crossings is within a physiologically plausible range (e.g., representing heart rates of between 30 and 200 beats per minute). Furthermore, in the case where there are many threshold values with similar crossing counts and variability statistics, the threshold with minimum absolute value is chosen, as this will tend to preserve low-amplitude true beats while possibly allowing a minimal amount of noise, which will be separated at later stages. FIG. 16 demonstrates the threshold 84 found by this algorithm on a 60 seconds long segment of ECG signal and several above-threshold beats 82.

Figure 17:
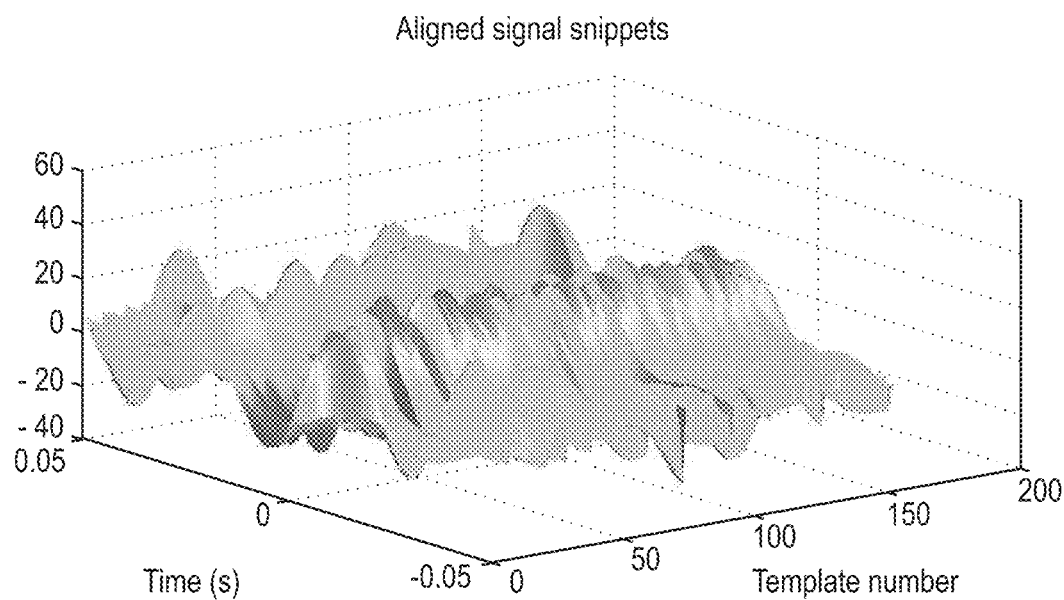
FIG. 17 illustrates the compilation of signal snippets surrounding the threshold crossings.

At S308, snippets of the filtered ECG are taken and list of threshold crossing 82 timings. For each threshold crossing, the portion of the signal immediately before and after the crossing (in these plots, this duration is 50 ms before to 50 ms after threshold crossing) is appended to a matrix, with each matrix row representing a potential PQRS cardiac complex, and aligned to the threshold crossing point. This is illustrated in FIG. 17, where each signal snippet surrounding a threshold crossing is plotted in time. In this plot one can see that many of the snippets have similar shapes—these are the desired cardiac complexes the algorithm is designed to isolate. In the embodiment, these crossing points 82 are used to capture 100 ms signal snippets. Other lengths of snippets are contemplated (e.g. 50 ms, 200 ms, 500 ms, and 1 sec).

Figure 18:
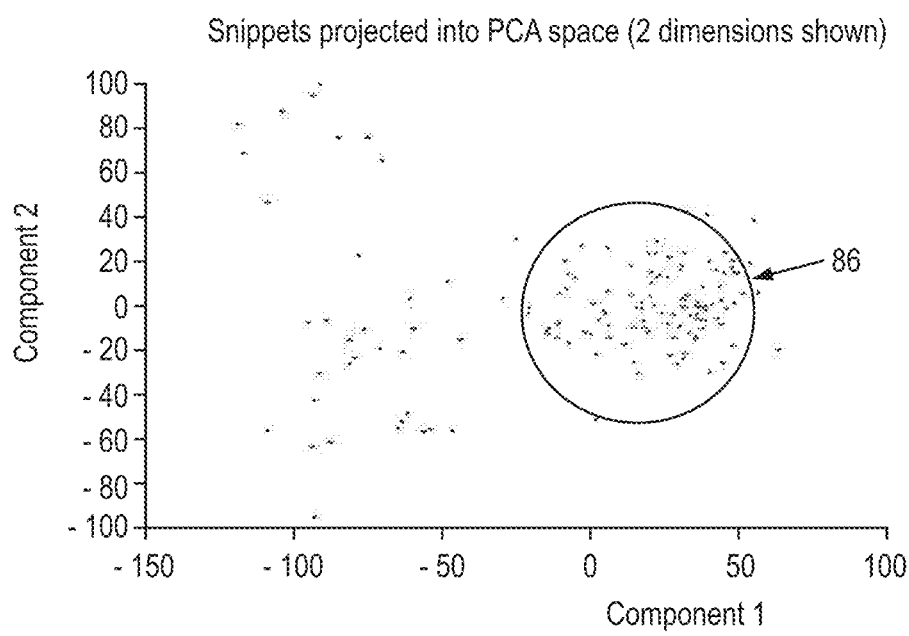
FIG. 18 illustrates the signal snippets represented in principal component analysis (PCA) space.

These f signal snippets (where f is the number of snippets) are used as rows in an f×g matrix, to which PCA is applied. The first n components are used to separate cardiac complexes from noise (in this embodiment, n=3, but other values are contemplated). This finds the ordered dimensions of maximum variation. FIG. 18 displays the signal snippets from FIG. 17 as points in this new PCA space. There should be a dense cluster representing true fQRS complexes that are similar to each other, and a more distributed set of points representing noise, which will tend to have large variation. The assumption for this analysis is that cardiac components will be more similar to each other than to noise, and that noise contributions will all be different. In this case, when cast into "PCA-space," the cardiac contributions form a discrete cluster 86 of a physiologically plausible number of units; whereas, the noise contributions will be distributed throughout the space.

At S310, the method proceeds with K-Means clustering to find the cluster that represents the fQRS complexes. The center of this cluster is used to assign a confidence value to each snippet by measuring the distance from the snippet to the center of the cluster. Snippets with points closer to the center of this cluster 86 are deemed more likely to be fQRS complexes than points farther away. That is, in one embodiment, the confidence is proportional to the inverse of the distance. This list of signal snippet times and confidences from each channel is then passed to the merging algorithm described below.

In one embodiment, k-means clustering is used, but other techniques such as hierarchical clustering, density-based, or distribution-based clustering could equivalently be employed. In the k-means case, the number of potential groups is varied from 1 to n (in this case 5). As this is a probabilistic technique, at each step number of groups the technique is repeated multiple times. At each iteration, each found cluster is evaluated based on the final heart rate, mean inter-R interval, and standard deviation of inter-R interval if the cluster were to represent true heart beats. At the end of this process, the cluster selected as the "true" cluster is the one that minimizes the standard deviation of inter-R intervals and is physiologically plausible (e.g., a heart rate between 30-200 bpm, or a more narrowly defined range if subject age is known). FIG. 18 displays the cluster that was determined to represent the cardiac complexes, where the circle 86 indicates highest density of points representing a true cardiac complex.

Figure 19:
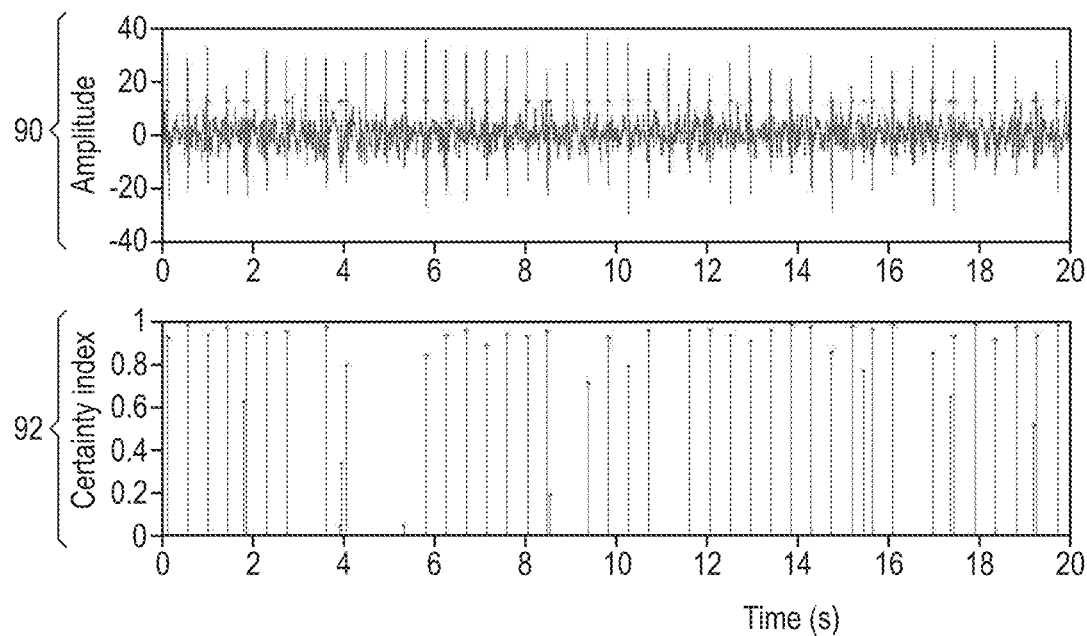
FIG. 19 illustrates the certainty of each heart beat based upon the original ECG trace.

At step or module S312, the cluster is used to identify which threshold crossings could be caused by heart beats and assign a confidence indication to each beat. This step makes use of the PCA clustering result in the following manner. The threshold crossings that have PCA representations near the center of the "true beat" cluster 86 are assumed to be true beats, and the distance from the center of that cluster is used as an indicator of reliability. Using the k-means based beat assignment, all beats assigned to the "true beat" cluster are included as potential beats. The standard deviation of the distances of these points from the center of the cluster is calculated, and this number is used to calculate a z-score of each point—each point's distance from the cluster center, normalized by the standard deviation of the cluster distances. This z-score is used as a reliability index, with lower z-scores (representing beats closer to the cluster center, and thus more stereotypical) indicating high-confidence beats. A top trace 90 of FIG. 19 shows the original ECG trace, now with potential heart beats identified. A bottom trace indicates 92 the confidence associated with each classification, where taller lines correspond to greater confidence.

Adaptive Rule Based Fetal QRS Identification (Step or Module S108 of FIG. 2)

Figure 20:
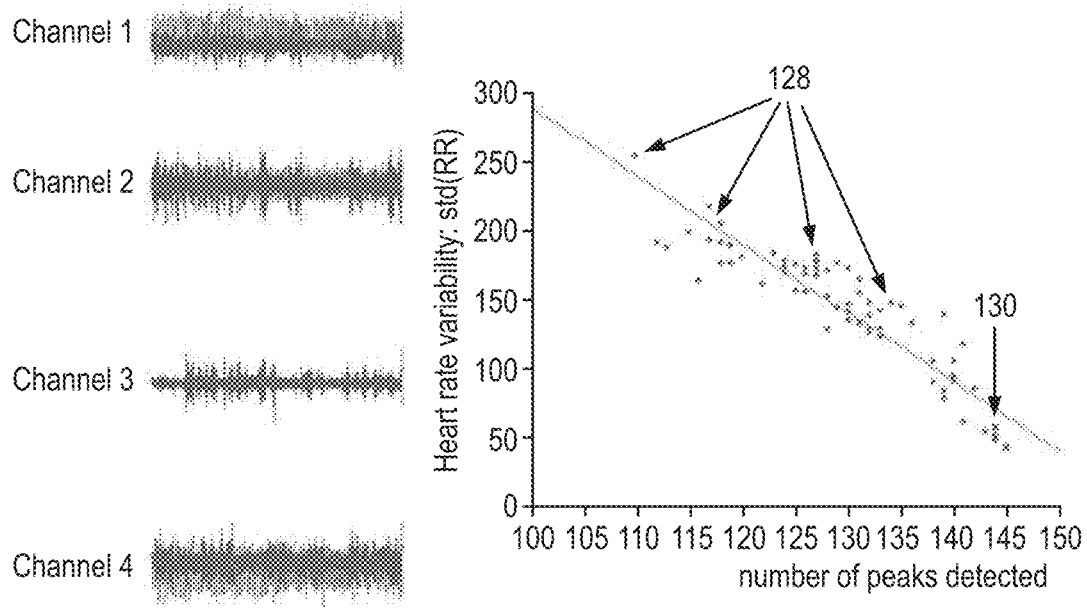
FIG. 20 illustrates finding the best combination of channels by considering the number of peaks and the resulting heart rate variability.

The best combination of channels or the polarity of the channel (direction of the R peak) can differ among recordings. To detect the R peaks, a basic peak detector is first applied to different combinations of channels and polarities. The different combinations are then ranked based on the number of peaks detected and heart rate variability. The combination of channel(s) with the most peaks detected and least heart rate variability is designated the winning combination whose peaks are then output as the fetal QRS locations. Possible combinations of channels are:

$$a*ch1+b*ch2+c*ch3+d*ch4$$

where a, b, c, and d can take on the values of 0, 1, and −1 resulting, for a four channel system, in 80 possible unique combinations, excluding [a,b,c,d]=[0, 0, 0, 0] since at least one channel must be used. The leading coefficient can be 1 and −1 because it is not known whether R peaks are going upward or downward (the polarity of the channel). One can decrease the set of possible combinations if there is confidence about the polarity of some of the channels. Peak detection is done on each combination of channels. To rank the different combinations, the number of peaks detected and the resulting heart rate variability (standard deviation of RR intervals) is measured. If the wrong polarity is used or if only channels with poor SNR are used, the resulting number of peaks and heart rate variability are likely to be poor. The winning combination should have a large number of peaks detected along with low heart rate variability, subject to biological constraints. These constraints could be different for maternal and fetal heart beats. FIG. 20 shows an example of this technique and how ranking of channel combinations are done. Each point 128 in FIG. 20 is projected onto the best fit line. The channel combination 130 resulting in the highest projected magnitude is the winning combination. In this particular record, the best combination of channels is (Ch1+Ch2+Ch3−Ch4) which means all channels contribute to a better peak detection. Channel 3 has low SNR but still provides some useful information. Removing channel 3 from the mix provides the second best solution. The best solution reverses the polarity of channel 4.

Calculating the required metrics for each channel can be computationally intensive. Less computationally intensive embodiments are contemplated. One can use shorter recordings (10 seconds instead of 1 minute recordings) to determine the best combination of channels and then apply the detected polarity to the entire record. One can use a subset of the 80 combinations such as only considering any combination of 2 channels. A simpler version of picking one out of 4 channels also yielded good results. In this case, the channel polarity is determined by applying peak detection to both the signal x and its negation −x and choosing the polarity that gives the largest median peak amplitudes. The best channel is then chosen as the one which gives the smallest heart rate variability.

Because fECG is often weak in abdominal recordings, almost all peak detectors will misplace some peaks or miss peaks completely. Therefore, it can be beneficial to make corrections to the output of peak detectors by estimating missing beats and shifting location of detected peaks. Applying the following two rules makes conservative corrections to the detected peaks with minimal alteration of peaks already correctly identified:

1) Missing beats are identified when the RR interval is greater than 1.3 times the median RR interval of the entire record. One or more new beats are then placed equally spread within neighboring peaks.

2) A peak is misplaced when a pair of RR intervals ($RR_k$, $RR_{k+1}$) shows one of the following patterns: (a) $RR_k \leq 0.9 \times medianRR$ followed by $RR_{k+1} \geq 1.1 \times medianRR$ or (b) $RR_k \geq 1.1 \times medianRR$ followed by $RR_{k+1} \leq 0.9 \times medianRR$. Misplaced peaks are shifted to midway between neighboring peaks.

These two rules make conservative corrections to the detected peaks with minimal alteration of peaks already correctly identified. A similar approach can be used to remove extra peaks. However, in the illustrated embodiment, extra peaks were not removed because not many extra beats were detected. FIGS. 21-23 provides an example of how these rules can improve peak detection.

FIG. 21 shows an RR interval before and after correction. Peaks 134 are possibly misplaced and peaks 132 are possibly missing. FIG. 22 shows an RR interval when missing beats are likely (upper chart) and the lower diagram shows the beat filled in. FIG. 23 shows the RR interval when peaks are misidentified (upper) and the peak shifted to a more likely location (lower). The dashed vertical lines in the upper charts denote estimates of fetal peak locations before correction. The dashed vertical lines denote estimates of fetal peak locations after correction in the lower chart.

The list of peak times may be assigned a standard confidence based on past performance of the method and then passed to the merging algorithm described below, with or without peaks from the PCA algorithm.

Merge Fetal QRS

Merge fQRS is designed to account for the fact that no single channel or method will be the best in all situations. Given a list of proposed fQRS locations from multiple sources, Merge fQRS implements a modified voting routine to determine likely fQRS complexes, which it then analyzes for likely missed and misplaced complexes. The first step in the algorithm is to create a zero-filled vector of the same duration as the ECG recordings (e.g., one minute each). Each input beat list is considered in turn, through a process in which the beat with the maximum certainty is chosen and its confidence metric is added to the vector. Chosen beats are removed from the channel's list until no beats remain, and the next list is added in the same manner to the vector. Strong fetal complexes should be recorded by multiple channels, and so contributions in corresponding bins should add. To account for timing variations, the signal is filtered by a Gaussian window prior to further analysis. The next step proceeds as the first—the tallest peak in the recording is held as the location of the highest confidence of a complex and is chosen first, its time is added to a list, and the region surrounding it is set to zero. The next highest peak is chosen and similarly added. This process repeats until the maximum peaks are less than 50% of the original maximum. After that point, a filling and shifting process similar to that described in Adaptive Rule Based fQRS is employed to bring the record in line with physiological statistics.

Figure 24:
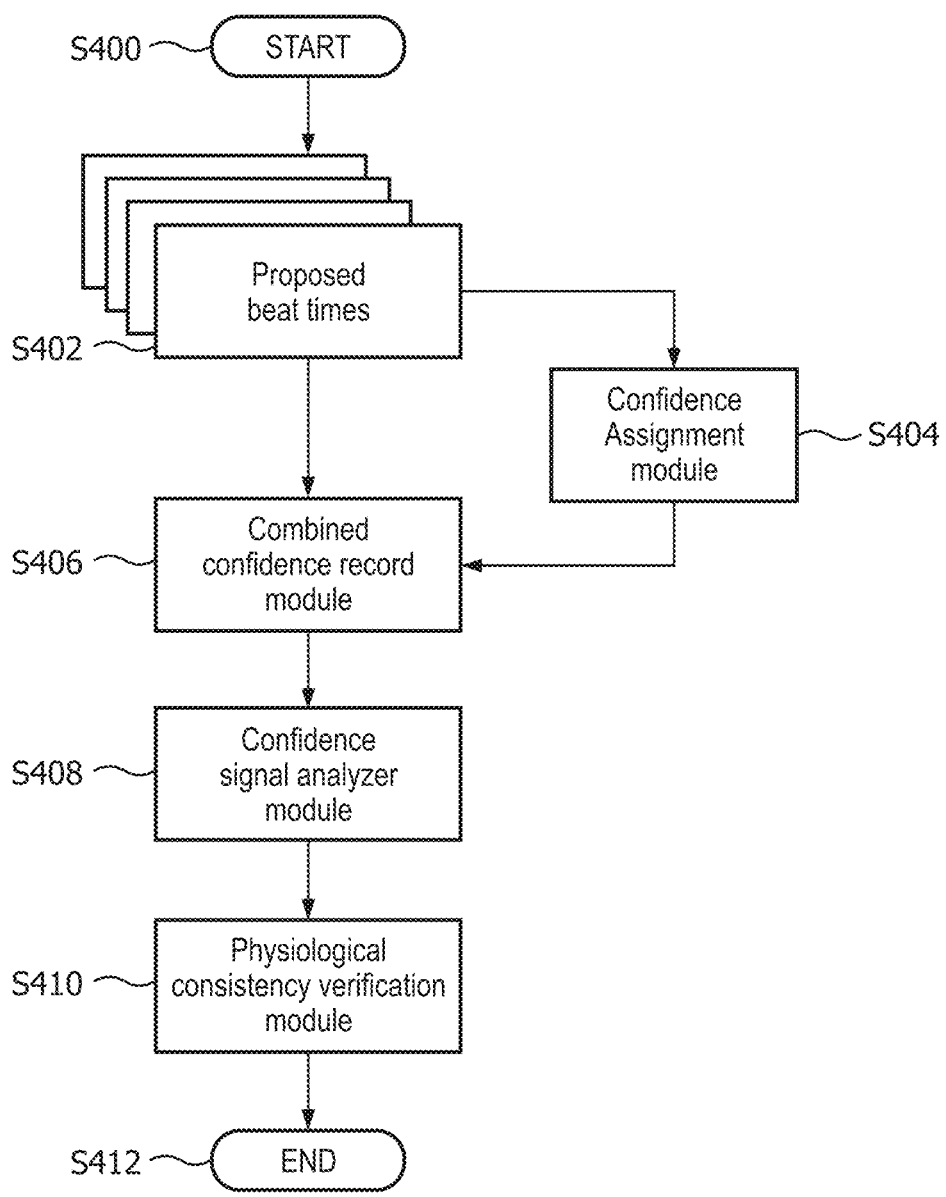
FIG. 24 illustrates a flowchart diagram depicting a merge process for the different signals or different results of processing the signals that is used to combine the output to get an accurate fetal QRS location.

FIG. 24 illustrates the sub-steps or sub-modules of step or module S110 of FIG. 2.

Step S110 starts at sub-step S400.

At S402, proposed timings of cardiac complexes from a recording session are received from the result of the multiple methods of step or module S108 (PCA-based or rule based beat detection) analyzing the same ECG trace. A more traditional beat detection algorithm such as "Local Max" may also be used as an input. The output may also be from the same method (e.g., PCA) being applied to multiple simultaneously recorded ECG channels. In one embodiment, a combination of these approaches is the input: multiple algorithms (PCA and rule based) are each applied to multiple ECG channels.

If the input algorithm provides a metric of confidence in each beat, that can be used. In the absence of such metrics, then, at S404, a confidence metric is assigned. This may be done three ways. A constant metric for all proposed beats from that source channel/algorithm, based either on a channel reliability metric (e.g. power spectrum analysis), or on relative performance of the analysis algorithm on existing training datasets may be assigned. A varying beat-by-beat metric where high confidence values are assigned to beats found in relatively low-noise segments, and lower confidences assigned to beats proposed in high-noise signal segments may be assigned. A combination of the two approaches may be used where a beat-by-beat confidence is assigned, but a maximum confidence possible is set by the expected reliability of the analysis technique or by the overall channel signal-to-noise ratio.

At S406, a combined confidence record that reflects the information from all input channels is initialized to zero. One input record is chosen (for example, at random) and the highest assigned confidence is added to the combined record at the corresponding time. The beat time that was added is removed from the input record, along with any nearby beat time. Here, nearby is set to the longest physiologically plausible interval, normally any beat time with 25 ms of the chosen beat time, corresponding to a heart rate of 40 bps. This interval can be tuned based on the statistics of the patient. In one embodiment, the interval is set to 12.5 ms, reflecting the fact that fetal heart rates are faster than adult heart rates. The next highest confidence is found and is added to the combined record, and it and nearby beat times are again removed. This process is repeated until no beats remain in the record. Once a record is empty, another input record is chosen at random and similarly added to the combined confidence record.

The newly created combined confidence record now consists of zeros where no input record assigned beat times, and non-zero values where input records assigned beats. At this point there can be some sections of the record that have only single proposed beats, and other regions with several nearby values where multiple input records proposed beats.

In order to accommodate imprecise timing between the different records, a Gaussian window is convolved against the combined record. This has the effect of creating a smooth confidence signal, where the height of the signal reflects increasing certainty of a true beat at this location. This is shown plot 110 of FIG. 25. This can be thought of as a voting procedure—areas of the record where multiple channels discovered a potential cardiac complex will have higher values than areas where only a single channel proposed as a beat location Similarly, the greater the temporal coincidence between beat proposals, the higher the summed Gaussian bumps.

At S408, this combined confidence signal is analyzed to discover beat locations that have either high confidence or high agreement between the channels. Similarly to how the combined record is constructed, the maximum point in the confidence signal is chosen as the first point to add to the proposed combined output record Once this point is chosen and added, the area near to the point is set to zero (following the interval width guidelines as described earlier). The next highest point in the combined confidence signal is chosen and added to the proposed combined output record, and the combined confidence signal is again zeroed near the chosen point. This process repeats, with the added constraint that when the algorithm attempts to add a point to a region of signal with more than 20 existing proposed beats in a minute segment, the added beat must be an approximate even multiple of the median inter-beat-time from the existing beats. A threshold of more or less than 20 may be used. The purpose of this constraint is to prevent the technique from adding low-confidence beats to the output record that are not physiologically plausible. Once the maximum of the confidence signal is less than 30% of the original maximum, this phase is complete.

At this point the maximum amount of information, has been extracted from each individual trace, but can still improve the output record by using common physiological assumptions.

At S410, by taking into account normal heart rate ranges and heart rate variability statistics, the technique finds violations of these statistics in its record and can optionally either provide an alert, annotate a likely error, or quietly correct the record, as appropriate in the application context. In one embodiment, the technique, similarly to the adaptive rule based step or module S108, searches for two main violations: record gaps, and beat misplacements. Record gaps occur when cardiac complexes are not detected by any of the input records. These gaps are found by measuring the median beat-to-beat interval of local sections of the signal, and then searching for areas of the signal that have a lack of beats over an interval approximately equal to an integer multiple of the local median beat-to-beat interval. These are marked as missing beats. The gap interval is used to assess the likely number of beats missed. The appropriate number of beats can be added to the record at the appropriate times. Beat misplacements can occur when beat timing is slightly off from where the true beat occurred. The signature of this type of error is when one beat-to-beat interval is greater (or less) than the local median interval time by a percentage, and the subsequent interval is less (or greater) than the median by the same percentage. The record is searched for this signature, and can adjust the beat timing in the appropriate direction to correct the issue.

At S412, the step or module S110 ends. The final output of S412 (and step or module S110) includes of the record of proposed times of cardiac complexes, along with the certainty associated (from the combined confidence signal), the input record identification with the "best version" of the beat, and indications of which beats have been added to fill gaps, or which beats have been adjusted to correct for timing errors. This final output is used to render display a heartbeat to a user. The bottom trace 110 of FIG. 25 shows the output record with solid vertical lines, which align closely with a cardiologist's annotations of true fetal cardiac complex locations, marked by dashed lines.

Figure 25:
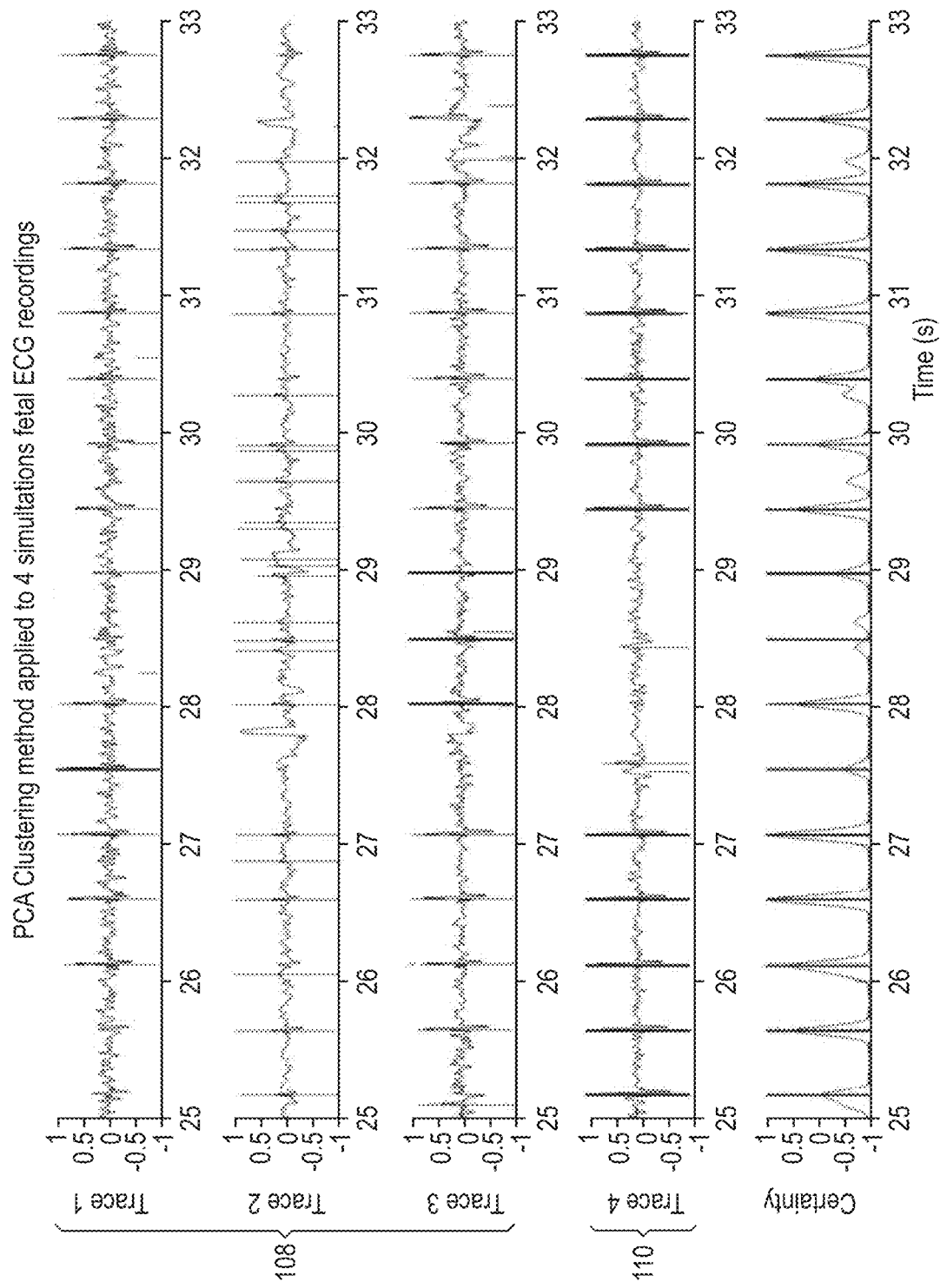
FIG. 25 illustrates four simultaneously-recorded Fetal ECG signals (see top four plots) and a combined confidence signal output (see bottom plot).

In this embodiment of FIG. 25, the technique was used for to create an output of one method (PCA-based beat detector) applied to 4 signals 108 of an input maternal (abdominal) ECG. The method could also combine the output from a PCA based beat detector with the output from alternate algorithms to provide a final combined beat record. The combined output of PCA and rule based detection (following PCA and OP maternal attenuation) generally out-performs the outputs of the component methods.

Results and Discussion

The results of three different techniques on sample data sets are shown in Table 1. A combination of these three algorithms yielded improved scores on the training datasets. Thus merging the three methods would be expected to improve performance on the validation set B, which did indeed yield improved results: 52.49 and 10.61 for Events 4 and 5 respectively. The methods used where PCA-PCA (PCA-maternal attenuation followed by PCA-clustering based fQRS), PCA-Adaptive (PCA-maternal attenuation followed by Adaptive rule based fQRS), and OP-Adaptive (OP-maternal attenuation followed by Adaptive rule based fQRS detection). Though the proposed spatial filtering techniques (PCA and OP) attenuate the maternal ECG, there could still be scenarios of maternal cardiac residues. The process of filling and shifting fetal QRS locations is meant to produce heart rate estimates that are physiological. However, this process may not produce true fetal QRS locations.

TABLE 1

|  | Sample A | | Sample A-ext | |
| --- | --- | --- | --- | --- |
|  | Event 4 | Event 5 | Event 4 | Event 5 |
| PCA-PCA | 64.35 | 9.94 | 248.27 | 18.68 |
| PCA-Adaptive | 7.02 | 4.29 | 165.28 | 14.11 |
| OP-Adaptive | 12.70 | 6.82 | 243.55 | 17.91 |
| Merge | 5.00 | 4.05 | 146.76 | 14.65 |

The invention has been described with reference to the preferred embodiments. Modifications and alterations may occur to others upon reading and understanding the preceding detailed description. It is intended that the invention be constructed as including all such modification and alterations insofar as they come within the score of the appended claims or the equivalents thereof.

The invention claimed is:

1. A system for extracting a fetal heart rate from a measured ECG signal, the measured ECG signal including a fetal ECG signal, a maternal ECG signal, and noise, the system comprising:
 a display; and
 at least one computer processor programmed to:
  receive abdominal ECG signals from at least one sensor attached to a patient;
  record and digitize each measured ECG signal in a measured ECG signal buffer;
  execute instructions stored in an instruction memory including:
   a peak detector configured to identify candidate peaks in the measured ECG signal buffer;
   a signal stacker configured to stack and divide the digitized measured ECG signals recorded in the signal buffer into a plurality of m snippets, each snippet including one candidate peak and including n samples, and to arrange the m snippets as a stacked matrix M with dimensions m×n;
   a spatial filter configured to identify and attenuate a maternal QRS signal in the plurality of m snippets of the measured ECG signal buffer by applying orthogonal projection to the stacked matrix M, to produce a raw fetal ECG signal which is stored in a raw fetal ECG buffer;
   a fetal QRS identifier configured to identify peaks in the raw fetal ECG buffer by at least one of principal component analysis and a peak-detection, and to use a rule based fQRS extraction to identify the peaks in the raw fetal ECG signal; and
   a merger configured to merge the identified peaks into the fetal ECG signal and to calculate the fetal heart rate from the identified peaks; and
  display the calculated fetal heart rate on the display.

2. The system according to claim 1, wherein the peak detector to identify candidate peaks includes:
 identifying a plurality of local maxima, eliminating local maxima having a derivative below a threshold, and checking a rate of the candidate peaks for physiological plausibility as a maternal heart rate.

3. The system according to claim 1, wherein the spatial filter includes principal component analysis, the identifying and attenuating of the maternal QRS including:
 stacking the snippets;
 calculating the mean of the snippets and one, two, or three of the next principal components;
 identifying the mean of the snippets as a main maternal component and identify the next one, two, or three principal components as other maternal components;
 attenuating the main maternal component and attenuate the other maternal components.

4. A method of extracting a fetal heart rate from at least one measured ECG signal, the measured ECG signal including a maternal ECG signal, a fetal ECG signal, and noise, the method comprising:
 recording and digitizing each measured ECG in a measured ECG signal buffer;
 identifying candidate peaks in the measured ECG signal;
 dividing the at least one measured ECG signal in the measured ECG buffer into a plurality of m snippets, each snippet including one candidate peak and including n samples;
 arranging the m snippets as a stacked matric M with dimensions m×n;

identifying and attenuating by spatial filtering a maternal QRS signal in the plurality of m snippets of the measured ECG signal buffer, the spatial filtering including applying orthogonal projection to the stacked matrix M, the spatial filtering producing a raw fetal ECG signal which is stored in a raw fetal ECG buffer, the orthogonal projection including repeating, until the maximum amplitude of the plurality of snippets is less than background:
extracting a normal vector of a maximum vector in the snippets; and
projecting the normal vector out of the snippets by orthogonalization;
identifying peaks in the raw fetal ECG signal by at least one of (1) principal component analysis and (2) peak-detection;
performing rule based fQRS extraction to identify fetal peaks in the raw ECG signal; and
calculating the fetal heart rate from the identified peaks; and
displaying the fetal heart rate on a display.

5. The method according to claim 4, wherein identifying the candidate peaks includes:
identifying a plurality of local maxima, eliminating local maxima having a derivative below a threshold, and checking a rate of the candidate peaks for physiological plausibility as a maternal heart rate.

6. The method according to claim 4, wherein the identifying and attenuating of the maternal QRS during the spatial filtering includes one of:
principal component analysis, including: stacking the snippets; calculating the mean of the snippets and, calculating one, two, or three of the next principal components; identifying the mean of the snippets as a main maternal component and, identifying the next one, two, or three principal components as other maternal components; attenuating the main maternal component and attenuating the other maternal components;
or orthogonal projection, including:
repeating, until the maximum amplitude of the plurality of snippets is less than background the steps of:
extracting a normal vector of a maximum vector in the snippets; and
projecting the normal vector out of the snippets by orthogonalization.

7. The method according to anyone of claim 4, wherein the spatial filtering includes orthogonal projection, the identifying and attenuating of the maternal QRS including:
repeating, until the maximum amplitude of the plurality of snippets is less than background:
extracting a norm vector of a maximum vector in the snippets; and
projecting the norm vector out of the snippets by orthogonalization.

8. A module for extracting a fetal heart rate from at least one maternal signal, the module comprising:
a processor configured to:
identify candidate peaks in at least one maternal signal buffer;
divide the at least one maternal signal buffer into a plurality of m snippets, each snippet including one candidate peak and including n samples;
arrange the m snippets as a stacked matrix M with dimensions m×n;
identify and attenuate by spatial filtering a maternal QRS signal in the plurality of snippets of each maternal signal buffering using a spatial filter, the spatial filter including at least one of principal component analysis and orthogonal projection applied to the stacked matrix M, the spatial filtering producing a raw fetal ECG signal which is stored in a raw fetal ECG buffer; and
identify peaks in the raw fetal ECG buffer by at least one of principal component analysis and a peak-detector followed by rule based fQRS extraction;
a recorder and digitizer which records and digitizes at least one maternal signal in a maternal signal buffer; and
a calculator for calculating the fetal heart rate from the identified peaks.

9. The system according to claim 1, wherein the at least one computer processor is programmed to use the peak detector to identify candidate peaks by operations including:
identifying a plurality of local maxima;
eliminating local maxima having a derivative below a threshold; and
checking a rate of the candidate peaks for physiological plausibility as a maternal heart rate.

10. The method according to claim 4, wherein the spatial filtering includes orthogonal projection, the identifying and attenuating of the maternal QRS including:
repeating, until the maximum amplitude of the plurality of snippets is less than background:
extracting a norm vector of a maximum vector in the snippets; and
projecting the norm vector out of the snippets by orthogonalization.

11. The fetal heart rate monitor of claim 8, wherein the recorder and digitizer comprise one or more A/D converter digitizers configured to digitize abdominal ECG signals from sensors attached to a patient.

* * * * *